US010415056B2

(12) United States Patent
Miller et al.

(10) Patent No.: US 10,415,056 B2
(45) Date of Patent: Sep. 17, 2019

(54) COMPOSITIONS AND METHODS FOR GENERATING ADENO-ASSOCIATED VIRAL VECTORS WITH UNDETECTABLE CAPSID GENE CONTAMINATION

(75) Inventors: Arthur Dusty Miller, Sisters, OR (US); Christine L. Halbert, Bothell, WA (US); Michael J. Metzger, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 882 days.

(21) Appl. No.: 13/884,914

(22) PCT Filed: Nov. 10, 2011

(86) PCT No.: PCT/US2011/060193
§ 371 (c)(1),
(2), (4) Date: Jul. 26, 2013

(87) PCT Pub. No.: WO2012/064960
PCT Pub. Date: May 18, 2012

(65) Prior Publication Data
US 2013/0296409 A1 Nov. 7, 2013

Related U.S. Application Data

(60) Provisional application No. 61/412,237, filed on Nov. 10, 2010.

(51) Int. Cl.
C12N 7/02 (2006.01)
C12N 15/86 (2006.01)
(52) U.S. Cl.
CPC .............. *C12N 15/86* (2013.01); *C12N 7/02* (2013.01); *C12N 2750/14143* (2013.01); *C12N 2750/14151* (2013.01)
(58) Field of Classification Search
CPC . C12N 7/02; C12N 2750/14151; C12N 15/86
See application file for complete search history.

(56) References Cited

U.S. PATENT DOCUMENTS

| 6,541,258 B2 | 4/2003 | Allen |
| 7,208,315 B2* | 4/2007 | Miller ........................ 424/233.1 |
| 2010/0047174 A1 | 2/2010 | Kay |

FOREIGN PATENT DOCUMENTS

WO 98/27204 A2 6/1998

OTHER PUBLICATIONS

Palomeque et al (Gene Therapy, 14: 989-997, 2007; (Year: 2007).*
Duan et al (Methods in Molecular Biology, Part of the Methods in Molecular Biology book series (MIMB, vol. 219) by Metzger, vol. 219: p. 29-51,2003). (Year: 2003).*
Weber, M., et al., "Recombinant Adeno-Associated Virus Serotype 4 Mediates Unique and Exclusive Long-Term Transduction of Retinal Pigmented Epithelium in Rat, Dog, and Nonhuman Primate After Subretinal Delivery," Molecular Therapy 7(6):774-781, Jun. 2003.
Weger, S., et al., "Control of Adeno-Associated Virus Type 2 Cap Gene Expression: Relative Influence of Helper Virus, Terminal Repeats, and Rep Proteins," Journal of Virology 71(11):8437-8447, Nov. 1997.
Wu, Z., et al., "Effect of Genome Size on AAV Vector Packaging," Molecular Therapy 18(1):80-86, Jan. 2010.
Xiao, X., et al., "Production of High-Titer Recombinant Adeno-Associated Virus Vectors in the Absence of Helper Adenovirus," Journal of Virology 72(3):2224-2232, Mar. 1998.
International Search Report dated May 23, 2012, issued in the corresponding International Application No. PCT/US2011/060193, filed Nov. 10, 2011, 5 pages.
International Preliminary Report on Patentability and Written Opinion dated May 14, 2013, issued in the corresponding International Application No. PCT/US2011/060193, filed Nov. 10, 2011, 6 pages.
Allen, J.M., et al., "Identification and Elimination of Replication-Competent Adeno-Associated Virus (AAV) That Can Arise by Nonhomologous Recombination During AAV Vector Production," Journal of Virology 71(9):6816-6822, Sep. 1997.
Allen, J.M., et al., "Improved Adeno-Associated Virus Vector Production With Transfection of a Single Helper Adenovirus Gene, E4orf6," Molecular Therapy 1(1 ):88-95, Jan. 2000.
Ayuso, E., et al., "High AAV Vector Purity Results in Serotype- and Tissue-Independent Enhancement of Transduction Efficiency," Gene Therapy 17(4):503-510, Apr. 2010.
Beaton, A., et al., "Expression From the Adeno-Associated Virus p5 and p19 Promoters Is Negatively Regulated in trans by the rep Protein," Journal of Virology 63(10):4450-4454, Oct. 1989.
Boissy, R., and C.R. Astell, "An *Escherichia coli* recBCsbcBrecF Host Permits the Deletion-Resistant Propagation of Plasmid Clones Containing the 5'-Terminal Palindrome of Minute Virus of Mice," Gene 35(1-2):179-185, 1985.
Cao, L., et al., "High-Titer, Wild-Type Free Recombinant Adeno-Associated Virus Vector Production Using Intron-Containing Helper Plasmids," Journal of Virology 74(24):11456-11463, Dec. 2000.
Cassinotti, P., et al., "Organization of the Adeno-Associated Virus (AAV) Capsid Gene: Mapping of a Minor Spliced mRNA Coding for Virus Capsid Protein," Virology 167(1):176-184, Nov. 1988.
Chadeuf, G., et al., "Efficient Recombinant Adeno-Associated Virus Production by a Stable Rep-Cap HeLa Cell Line Correlates With Adenovirus-Induced Amplification of the Integrated Rep-Cap Genome," Journal of Gene Medicine 2(4):260-268, Jul.-Aug. 2000.
Chadeuf, G., et al., "Evidence for Encapsidation of Prokaryotic Sequences During Recombinant Adeno-Associated Virus Production and Their in Vivo Persistence After Vector Delivery," Molecular Therapy 12(4):744-753, Oct. 2005.

(Continued)

*Primary Examiner* — Anoop S Singh
*Assistant Examiner* — Magdalene K Sgagias
(74) *Attorney, Agent, or Firm* — Christensen O'Connor Johnson Kindness PLLC

(57) ABSTRACT

In one aspect, the present invention provides an intron-modified cap expression cassette useful for generating adeno-associated virus (AAV) vector particles. In another aspect, the present invention provides a method of reducing the immune response in a mammalian subject undergoing treatment with an AAV vector.

12 Claims, 4 Drawing Sheets
Specification includes a Sequence Listing.

(56) References Cited

OTHER PUBLICATIONS

Chang, L.S., et al "Adeno-Associated Virus P5 Promoter Contains an Adenovirus E1A-Inducible Element and a Binding Site for the Major Late Transcription Factor," Journal of Virology 63(8):3479-2488, Aug. 1989.

Chen, J., et al., "Determination of Specific CD4 and CD8 T Cell Epitopes After AAV2- and AAV8-hF.IX Gene Therapy," Molecular Therapy 13(2):260-269, Feb. 2006.

Chen, H., "Intron Splicing-Mediated Expression of AAV Rep and Cap Genes," Molecular Therapy 16(5):924-30, May 2008.

Dong, B., et al., "Characterization of Genome Integrity for Oversized Recombinant AAV Vector," Molecular Therapy 18(1):87-92, Jan. 2010.

Duan, D., et al., "Expanding AAV Packaging Capacity With Trans-Splicing or Overlapping Vectors: A Quantitative Comparison," Molecular Therapy 4(4):383-391, Oct. 2001.

Graham, F.L., et al., "Characteristics of a Human Cell Line Transformed by DNA From Human Adenovirus Type 5," Journal of General Virology 36(1):59-74, Jul. 1977.

Gregorevic, P., et al., "Systemic Delivery of Genes to Striated Muscles Using Adeno-Associated Viral Vectors," Nature Medicine 10(8):828-834, Aug. 2004.

Halbert, C.L., and A.D. Miller, "AAV-Mediated Gene Transfer to Mouse Lungs," Methods in Molecular Biology 246:201-212, 2004.

Halbert, C.L., et al., "Expression of Human α1-Antitrypsin in Mice and Dogs Following AAV6 Vector-Mediated Gene Transfer to the Lungs," Molecular Therapy 18(6):1165-1172, Jun. 2010.

Halbert, C.L., et al., "Adeno-Associated Virus Type 6 (AAV6) Vectors Mediate Efficient Transduction of Airway Epithelial Cells in Mouse Lungs Compared to That of AAV2 Vectors," Journal of Virology 75(14):6615-6624, Jul. 2001.

Halbert, C.L., et al., "Efficient Mouse Airway Transduction Following Recombination Between AAV Vectors Carrying Parts of a Larger Gene," Nature Biotechnology 20(7):697-701, Jul. 2002.

Halbert, C.L., et al., "Transduction by Adeno-Associated Virus Vectors in the Rabbit Airway: Efficiency, Persistence, and Readministration," Journal of Virology 71(8):5932-5941, Aug. 1997.

Halbert, C.L., et al., "High-Efficiency Promoter-Dependent Transduction by Adeno-Associated Virus Type 6 Vectors in Mouse Lung," Human Gene Therapy 18(4):344-354, Apr. 2007.

Hauck, B., et al., "Undetectable Transcription of Cap in a Clinical AAV Vector: Implications for Preformed Capsid in Immune Responses," Molecular Therapy 17(1):144-152, Jan. 2009.

Herzog, R.W., et al., "Long-Term Correction of Canine Hemophilia B by Gene Transfer of Blood Coagulation Factor IX Mediated by Adeno-Associated Viral Vector," Nature Medicine 5(1):56-63, Jan. 1999.

Hörer, M., et al., "Mutational Analysis of Adeno-Associated Virus Rep Protein-Mediated Inhibition of Heterologous and Homologous Promoters," Journal of Virology 69(9):5485-5496, Sep. 1995.

Jay, F.T., et al., "Eukaryotic Translational Control: Adeno-Associated Virus Protein Synthesis Is Affected by a Mutation in the Adenovirus DNA-Binding Protein," Proceedings of the National Academy of Sciences of the United States of America (PNAS) 78(5):2927-2931, May 1981.

Kyöstiö, S.R., et al., "Negative Regulation of the Adeno-Associated Virus (AAV) P5 Promoter Involves Both the P5 Rep Binding Site and the Consensus ATP-Binding Motif of the AAV Rep68 Protein," Journal of Virology 69(11):6787-6796, Nov. 1995.

Lai, Y., et al., "Evidence for the Failure of Adeno-Associated Virus Serotype 5 to Package a Viral Genome > or = 8.2 kb," Molecular Therapy 18(1):75-79, Jan. 2010.

Lewis, B.A., "Adenovirus E1A Proteins Interact With the Cellular YY1 Transcription Factor," Journal of Virology 69(3):1628-1636, Mar. 1995.

Li, J. et al., "Role for Highly Regulated Rep Gene Expression in Adeno-Associated Virus Vector Production," Journal of Virology 71(7):5236-5243, Jul. 1997.

Liu, X., et al., "Selective Rep-Cap Gene Amplification as a Mechanism for High-Titer Recombinant AAV Production From Stable Cell Lines," Molecular Therapy 2(4):394-403, Oct. 2000.

Manno, C.S., et al., "Successful Transduction of Liver in Hemophilia by AAV-Factor IX and Limitations Imposed by the Host Immune Response," Nature Medicine 12(3):342-347, Mar. 2006.

Matsushita, T., et al., "Adeno-Associated Virus Vectors Can Be Efficiently Produced Without Helper Virus," Gene Therapy 5(7):938-945, Jul. 1998.

McCarty, D.M., et al., "Sequences Required for Coordinate Induction of Adeno-Associated Virus P19 and P40 Promoters by Rep Protein," Journal of Virology 65(6):2936-2945, Jun. 1991.

Mingozzi, F., et al., "AAV-1—Mediated Gene Transfer to Skeletal Muscle in Humans Results in Dose-Dependent Activation of Capsid-Specific T Cells," Blood 114(10):2077-2086, Sep. 2009.

Mochizuki, S., et al., "Long-Term Correction of Hyperphenylalaninemia by AAV-Mediated Gene Transfer Leads to Behavioral Recovery in Phenylketonuria Mice," Gene Therapy 11(13):1081-1086, Jul. 2004.

Muzyczka, N., "Use of Adeno-Associated Virus as a General Transduction Vector for Mammalian Cells," Current Topics in Microbiology and Immunology 158:97-129, 1992.

Ni, T.H., et al., "Cellular Proteins Required for Adeno-Associated Virus DNA Replication in the Absence of Adenovirus Coinfection," Journal of Virology 72(4):2777-2787, Apr. 1998.

Nony, P., et al., "Evidence for Packaging of Rep-Cap Sequences Into Adeno-Associated Virus (AAV) Type 2 Capsids in the Absence of Inverted Terminal Repeats: A Model for Generation of Rep-Positive AAV Particles," Journal of Virology 77(1):776-781, Jan. 2003.

Passini, M.A., et al., "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," Journal of Virology 77(12):7034-7040, Jun. 2003.

Salvetti, A., et al., "Factors Influencing Recombinant Adeno-Associated Virus Production," Human Gene Therapy 9(5):695-706, Mar. 1998.

Samulski, R.J., et al., "Helper-Free Stocks of Recombinant Adeno-Associated Viruses: Normal Integration Does Not Require Viral Gene Expression," Journal of Virology 63(9):3822-3828, Sep. 1989.

Shi, Y., et al., "Transcriptional Repression by YY1, a Human GLI-Krüppel-Related Protein, and Relief of Repression by Adenovirus E1A Protein," Cell 67(2):377-388, Oct. 1991.

Smith, R., et al., "A Simplified Baculovirus-AAV Expression Vector System Coupled With One-Step Affinity Purification Yields High-Titer rAAV Stocks From Insect Cells," Molecular Therapy 17(11):1888-96, Nov. 2009.

Stieger, K., et al., "Detection of Intact rAAV Particles Up to 6 Years After Successful Gene Transfer in the Retina of Dogs and Primates," Molecular Therapy 17(3):516-523, Mar. 2009.

Tratschin, J.D., et al., "Negative and Positive Regulation in Trans of Gene Expression From Adeno-Associated Virus Vectors in Mammalian Cells by a Viral Rep Gene Product," Molecular Cell Biology 6(8):2884-2894, Aug. 1986.

Trempe, J.P., and B.J. Carter, "Alternate mRNA Splicing Is Required for Synthesis of Adeno-Associated Virus VP1 Capsid Protein," Journal of Virology 62(9):3356-3363, Sep. 1988.

Wang, X.S., et al., "Characterization of Wild-Type Adeno-Associated Virus Type 2-Like Particles Generated During Recombinant Viral Vector Production and Strategies for Their Elimination," Journal of Virology 72(7):5472-5480, Jul. 1998.

Wang, Z., et al., "Immunity to Adeno-Associated Virus-Mediated Gene Transfer in a Random-Bred Canine Model of Duchenne Muscular Dystrophy," Human Gene Therapy 18(1):18-26, Jan. 2007.

Wang, Z., et al., "Sustained AAV-Mediated Dystrophin Expression in a Canine Model of Duchenne Muscular Dystrophy With a Brief Course of Immunosuppression," Molecular Therapy 15(6):1160-1166, Jun. 2007.

\* cited by examiner

COMPOSITIONS AND METHODS FOR GENERATING ADENO-ASSOCIATED VIRAL VECTORS WITH UNDETECTABLE CAPSID GENE CONTAMINATION

CROSS-REFERENCE(S) TO RELATED APPLICATION(S)

This application claims the benefit of U.S. Provisional Application No. 61/412,237 filed on Nov. 10, 2010, the disclosure of which is hereby incorporated by reference in its entirety.

STATEMENT OF GOVERNMENT LICENSE RIGHTS

This invention was made with government support under DK047754, DE019582, and CA009229 awarded by the National Institutes of Health. The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is: 38154SEQ_FINAL_2011-11-08.txt. The file is 58 KB; was created on Nov. 8, 2011, and is being submitted via EFS-Web with the filing of the specification.

FIELD OF THE INVENTION

This invention relates to compositions and methods for generating adeno-associated viral (AAV) vectors.

BACKGROUND

The prototype wild type AAV genome (AAV type 2) is a 4,600 base single stranded DNA molecule including a terminal 145 base repeat sequence (ITR) at each end (Muzcyzka, Curr. Top. Microbiol. Immunol. 158:97-129, 1992). The AAV non-structural and structural open reading frames (ORFs) responsible for replication and encapsidation of the genome are derived from alternatively spliced transcripts originating from three distinct promoters. The replication (Rep) proteins are designated as Rep 78/68 and Rep 52/40, initiated at the P5 and P19 promoters, respectively. The structural capsid (Cap) proteins (VP1, VP2, and VP3) are under the control of the P40 promoter (Muzcyzka supra). A combination of the terminal repeats, cis-sequences proximal to the AAV promoters, Rep proteins, adenovirus gene products, and cellular factors are responsible for the appropriate expression of the AAV Rep and Cap proteins (Tratschin et al., *Mol. Cell. Biol.* 6:2884-2894 (1986); Beaton et al., *J. Virol.* 63:4450-4454 (1989); Chang et al., *J. Virol.* 63:3479-3488 (1989); McCarty et al., *J. Virol.* 65:2936-2945 (1991); Shi et al., *Cell* 67:377-388 (1991); Horer et al., *J. Virol.* 69:5484-5496 (1995); Kyostio et al., *J. Virol.* 69:6787-6796 (1995); Lewis et al., *J. Virol.* 69:1628-1636 (1995); Weger et al., *J. Virol.* 71:8437-8447 (1997); Ni et al., *J. Virol.* 72:2777-2787 (1998)).

Adeno-associated virus is a defective parvovirus that grows in cells in which certain functions are provided by a co-infecting helper virus. General reviews of AAV may be found in, for example, Carter, *Handbook of Parvoviruses*, Vol. I, pp. 169-228 (1989), and Berns, *Virology*, pp. 1743-1764, Raven Press, New York, N.Y. (1990), incorporated herein by reference. Examples of co-infecting viruses that provide helper functions for AAV growth and replication are adenoviruses, herpes viruses, and in some cases, poxviruses such as vaccinia. The nature of the helper function is not entirely understood, but it appears that the helper virus indirectly renders the cell permissive for AAV replication. This belief is supported by the observation that AAV replication may occur at low efficiency in the absence of helper virus co-infection if the cells are treated with agents that are either genotoxic or that disrupt the cell cycle.

Although AAV may replicate to a limited extent in the absence of helper virus in these unusual conditions, more generally infection of cells with AAV in the absence of helper functions results in the proviral AAV genome integrating into the host cell genome. If these cells are superinfected with a helper virus such as adenovirus, the integrated AAV genome can be rescued and replicated to yield a burst of infectious progeny AAV particles. The fact that integration of AAV appears to be efficient suggests that AAV would be a useful vector for introducing genes into cells for use, such as, in human gene therapy.

AAV has a very broad host range without any obvious species or tissue specificity and can replicate in virtually any cell line of human, simian or rodent origin provided that an appropriate helper is present. AAV is also relatively ubiquitous and has been isolated from a variety of animal species including most mammalian and several avian species.

AAV vectors including heterologous polynucleotide sequences flanked by the AAV terminal repeats (ITRs) can be assembled into virions when introduced into appropriate cells by transfection with packaging plasmids encoding the Rep and Cap reading frames, but lacking the ITRs, and by co-infection with the non-related helper adenovirus (Samulski et al., *J. Virol.* 63:3822-3828 (1989); Muzcyka, *Curr. Top. Microbiol. Immunol.* 158:97-129 (1992)).

Initial AAV packaging plasmids contained simple deletions of the packaging signal (ITRs) to supply the Rep and Cap proteins for AAV vector production without generating wild type virus (Samulski et al., supra (1989); Muzyczka, supra (1992)). The AAV/Ad packaging construct, for example, has been widely used to generate AAV vector stocks by co-transfection into human embryonic kidney 293 cells (Graham et al., *J. Virol.* 36:59-74 (1977); Samulski et al., *J. Virol.* 63:3822-3828 (1989)). A derivative packaging plasmid, ACG-2, was described which converted the Rep 78/68 initiation codon from AUG to ACG to reduce the level of Rep 78/68 expression (Li et al., *J. Virol.* 71:5236-5243 (1987)). Over expression of the Rep 78/68 proteins has been correlated with decreases in AAV vector production. Expression of the AAV reading frames from these plasmids is still dependent upon transcription from the AAV P5, P19, and P40 promoters.

Co-transfection of AAV/Ad and AAV vector plasmids has been shown to result in significant contamination of vector stocks with replication-competent AAV (rcAAV) presumably by recombination between the plasmids during transfection (Allen et al., *J. Virol.* 71:6816-6822 (1997); Salvetti et al., *Hum. Gene Ther.* 9:695-706 (1998); Wang et al., *J. Virol.* 72:5472-5480 (1998)). An AAV packaging plasmid has previously been described which split the AAV rep and cap genes, placing them in an inverted orientation relative to the wild type AAV, and replaced the P5 and P40 promoters with the mouse metallothionein and cytomegalovirus (CMV) regulatory sequences, respectively (MTrep/CMV-cap, see FIG. 1 of Allen et al., *J. Virol.* 71:6816-6822 (1997);

WO98/27204, each hereby incorporated herein by reference). AAV vector production with this packaging plasmid was comparable to levels of vector produced with the AAV/Ad packaging plasmid and was free of rcAAV. Production of AAV vector using MTrep/CMVcap was still enhanced by infection with helper adenovirus despite the substitution of the P5 and P40 promoter sequences.

Adenovirus infection is an easy and efficient method for supplying the helper activities necessary for AAV vector production. However, removal of adenovirus from AAV vector stocks is laborious and can result in the contamination of vector stocks with potentially immunoreactive adenovirus proteins. Recently it has been shown that the adenovirus activities required for AAV vector production can be supplied by transfection of 293 cells with plasmids containing the E2A, E4 and VA RNA genes (Xiao et al., *Journal of Virology*, 72:2224-2232 (1998); Matsushita et al., *Gene Ther.* 5:938-945 (1998)). Full helper activity required the transfection of all three transcription units (Matsushita et al., supra (1998), incorporated herein by reference).

There are at least two desirable features of any AAV vector designed for use in human gene therapy. First, the transducing vector must be generated at titers sufficiently high to be practicable as a delivery system. This is especially important for gene therapy strategies aimed at in vivo delivery of the vector. For example, it is likely that for many desirable applications of AAV vectors, such as treatment of cystic fibrosis by direct in vivo delivery to the airway, the required dose of transducing vector may be in excess of $10^{10}$ particles. Secondly, the vector preparations must be essentially free of wild type AAV virus (or any replication-competent AAV). The attainment of high titers of AAV vectors has been difficult for several reasons including preferential encapsidation of wild type AAV genomes (if they are present or generated by recombination), and the difficulty in generating sufficient complementing functions such as those provided by the wild type rep and cap genes. Useful cell lines expressing such complementing functions have been especially difficult to generate, in part because of pleiotropic inhibitory functions associated with the rep gene products. Thus, cells in which the rep gene is integrated and expressed tend to grow slowly or express Rep at very low levels.

Vectors based on adeno-associated viruses (AAV) have been used in many applications in vivo because they promote persistent gene expression in dividing and non-dividing cells in multiple somatic tissues of animals (see, e.g., Herzog R. W. et al., *Nat Med* 5:56-63 (1999); Passini M A et al., *J Virol* 77:7034-7040 (2003); Weber M et al., *Mol Ther* 7:774-781 (2003) and Mochizuki S et al., *Gene Ther* 11:1081-1086 (2004)). However, recent studies have shown that the lack of an immune response seen in many mouse and some large animal studies has not been duplicated in human trials. For example, in a clinical trial for hemophilia B, two of seven subjects given an AAV vector-expressing clotting factor IX (FIX) developed a transient self-limiting increase in liver transaminases, followed by clearance of the FIX-expressing cells at 4 to 8 weeks after delivery (Manno, C. S., et al., *Nat. Med.* 12:342-347 (2006)). In this clinical trial for hemophilia B, a cytotoxic lymphocyte (CTL) response to AAV capsid but not to FIX was detected in peripheral blood mononuclear cells. In another clinical trial involving lipoprotein lipase, clearance of AAV-transduced cells coincided with a CTL response towards the capsid, but not the transgene (Mingozzi, F., et al., *Blood* 114:2077-2086 (2009)).

Therefore, a need exists for generating AAV vector preparations that reduce or eliminate the immune response in a mammalian subject.

SUMMARY

In one aspect, the present invention provides an intron-modified cap expression cassette useful for generating adeno-associated virus (AAV) vector particles. The intron-modified cap expression cassette comprises: (i) a nucleic acid molecule comprising a nucleotide sequence encoding AAV capsid protein operably linked to a promoter, wherein the encoded AAV capsid protein is capable of packaging AAV vectors in the presence of rep and adeno helper functions, and (ii) at least one heterologous intron sequence operably linked to the nucleotide sequence encoding the AAV capsid protein; wherein the total length of the expression cassette is at least 5 kilobases. In one embodiment, the invention provides a vector comprising the intron-modified cap expression cassette. In another embodiment, the invention provides a cell line comprising the intron-modified cap expression cassette.

In another aspect, the present invention provides a method of generating an expression cassette for producing adeno-associated virus (AAV) vectors, comprising inserting at least one heterologous intron sequence into a nucleic acid molecule comprising a nucleotide sequence encoding an AAV capsid protein operably linked to a promoter, wherein the total length of the expression cassette is at least 5 kilobases.

In another aspect, the present invention provides a method of reducing intact cap gene contamination in a population of AAV vector particles. The method comprises: (a) introducing an AAV vector into a suitable host cell comprising an intron-modified cap expression cassette; (b) expressing rep and adeno helper functions in the host cell; and (c) culturing the host cell to produce a population of AAV vector particles.

In another aspect, the present invention provides a method of reducing the immune response in a mammalian subject undergoing treatment with an AAV vector comprising administering to the mammalian subject a preparation of AAV vector particles comprising a nucleic acid sequence encoding a therapeutic molecule, wherein the preparation of AAV vector particles was produced with an intron-modified cap expression cassette, and wherein the immune response in the mammalian subject to the AAV vector generated using the intron-modified cap expression cassette is significantly reduced or absent as compared to the immune response generated with a preparation of AAV vector particles generated using a standard cap expression cassette.

In another aspect, the present invention provides a complementation assay for measuring the presence or amount of cap gene contamination in a preparation of AAV vector virions, the assay comprising: (a) infecting a host cell with a test preparation of AAV vector, wherein the host cell comprises: (i) an indicator AAV vector with a detectable marker, (ii) a rep expression vector, and (iii) adenovirus helper functions; (b) culturing the host cell for a period of time sufficient to generate AAV vector virions from the indicator AAV vector; (c) contacting an indicator cell with cell lysate obtained from the host cells cultured in accordance with step (b); and (d) determining the presence or amount of indicator cells that are positive for the detectable marker, wherein a positive result indicates that the test preparation of AAV vector virions contains cap gene contamination.

In another aspect, the present invention provides a complementation assay for measuring the presence or amount of rep gene contamination in a preparation of AAV vector virions, the assay comprising: (a) infecting a host cell with a test preparation of AAV vector, wherein the host cell comprises: (i) an indicator AAV vector with a detectable marker, (ii) a cap expression vector, and (iii) adenovirus helper functions; (b) culturing the host cell for a period of time sufficient to generate AAV vector virions from the indicator AAV vector; (c) contacting an indicator cell with cell lysate obtained from the host cells cultured in accordance with step (b); and (d) determining the presence or amount of indicator cells that are positive for the detectable marker, wherein a positive result indicates that the test preparation of AAV vector virions contains rep gene contamination.

As described herein, the compositions of the invention are useful for carrying out the methods of the invention.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DESCRIPTION OF SEQUENCE LISTING

Figure 1:
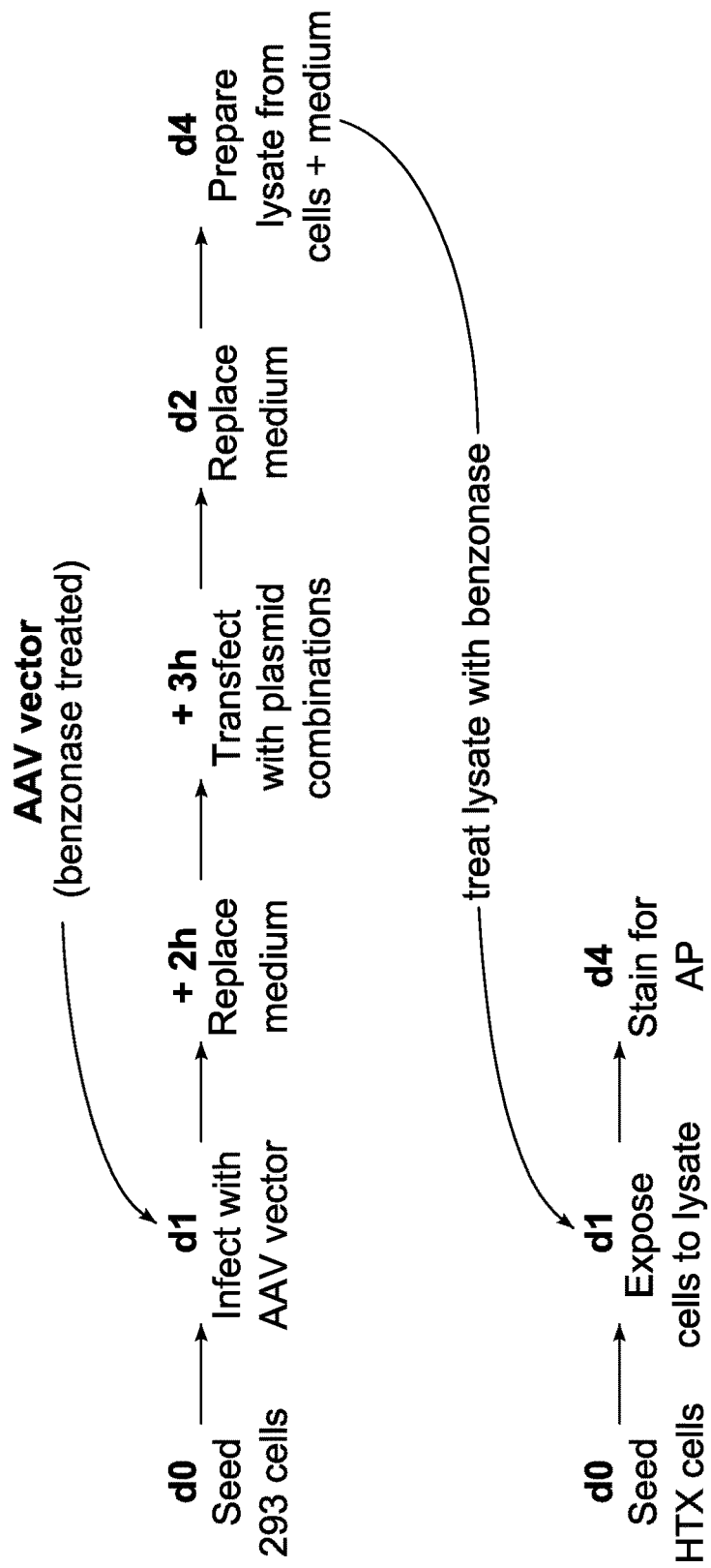
FIG. 1 is a flow diagram illustrating the steps of a cap and rep complementation assay, as described in Example 2.

SEQ ID NO:1 is the AAV-6 CAP ORF.
SEQ ID NO:2 is the AAV-6 Capsid protein encoded by SEQ ID NO:1;
SEQ ID NO:3 is a portion of the AAV-6 intron only including SA1 and SA2.
SEQ ID NO:4 is the AAV-6 intron including SA1 and SA2.
SEQ ID NO:5 is the EIF2S1 intron region 4285 nt.
SEQ ID NO:6 is the AAV-6 intron starting at SA1 through the CAP ORF.
SEQ ID NO:7 is the complete sequence of CMVE2cap6.
SEQ ID NO:8 is the AAV-2 cap ORF (CDS 2203-4410 from NC_001410.2).
SEQ ID NO:9 is the AAV-2 Capsid protein encoded by SEQ ID NO:8.
SEQ ID NO:10 is Rep forward primer.
SEQ ID NO:11 is Rep reverse R1 primer.
SEQ ID NO:12 is CapF forward primer.
SEQ ID NO:13 is CapR540 primer.
SEQ ID NO:14 is primer cFIXF1.
SEQ ID NO:15 is primer cFIXR2.
SEQ ID NO:16 is primer lacZqF1.
SEQ ID NO:17 is primer lacZqR1.
SEQ ID NO:18 is primer EIF2S1inFN.
SEQ ID NO:19 is primer EIF2S1inRN.

DETAILED DESCRIPTION

Unless specifically defined herein, all terms used herein have the same meaning as they would to one skilled in the art of the present invention. The practice of the subject matter described herein will employ, unless otherwise indicated, conventional techniques of molecular biology, microbiology, cell biology and recombinant DNA, which are within the skill of the art. See, e.g., Sambrook, Fritsch, and Maniatis, *Molecular Cloning: a Laboratory Manual, 2nd edition* (1989); *Current Protocols in Molecular Biology* (F. M. Ausubel et al. eds., 1987); the series *Methods in Enzymology* (Academic Press, Inc.); *PCR 2: A Practical Approach* (M. Jr McPherson, B. D. Hames, and G. R. Taylor, eds., 1995); and *Animal Cell Culture* (R. I. Freshney, ed., 1987).

The following definitions are provided in order to provide clarity with respect to the terms as they are used in the specification and claims to describe the present invention.

As used herein, the term "vector" is a nucleic acid molecule which transfers and/or replicates an inserted nucleic acid molecule into and/or between host cells. In some embodiments, the vectors of the invention are incapable of autonomous self-replication.

As used herein, the term "nucleic acid sequences allowing for autonomous replication" refers to a polynucleotide comprising an origin of replication (generally referred to as an ori sequence) which allows for replication of the polynucleotide in the appropriate host cell.

As used herein, the term "heterologous" means derived from a genotypically distinct entity from that of the rest of the entity to which it is compared. For example, a polynucleotide introduced by genetic engineering techniques into a different cell type is a heterologous polynucleotide. When that polynucleotide is expressed, the polynucleotide can encode a heterologous polypeptide.

As used herein, the term "operably linked" refers to a juxtaposition wherein the components so described are in a relationship permitting them to function in their intended manner. For example, a promoter sequence is operably linked to a coding sequence if the promoter sequence promotes transcription of the coding sequence. As another example, an intron sequence is operably linked to a transcriptional unit if the intron contains splice donor and splice acceptor sites allowing for proper splicing of the transcription unit. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous.

As used herein, the term "expression cassette" refers to a nucleic acid construct, generated recombinantly or synthetically, with a series of specified nucleic acid elements which permit transcription of a particular nucleic acid in a host cell. The expression cassette can be incorporated into a plasmid, chromosome, virus, or nucleic acid fragment.

As used herein, the term "percent identity" or "percent identical", refers to the percentage of amino acid residues in a polypeptide sequence, or nucleic acids in a nucleotide sequence that are identical with the amino acid sequence or nucleic acid sequence, respectively, of a specified molecule, after aligning the sequences to achieve the maximum percent identify. For example, the Vector NTI Advance™ 9.0 may be used for sequence alignment. Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, *Proc. Natl. Acad. Sci. USA* 87:2264-2268 (1990) and as discussed in Altschul et al., *J. Mol. Biol.* 215:403-410 (1990); Karlin and Altschul, *Proc. Natl. Acad. Sci. USA* 90:5873-5877 (1993); and Altschul et al., *Nucleic Acids Res.* 25:3389-3402 (1997). Ranges of desired degrees of sequence identity are approximately 80% to 100% and integer values there between. Typically, the percent identities between a disclosed sequence and a claimed sequence are at least 80%, at least 85%, at least 90%, at least 95%, or at least 98%.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80-85%, preferably 85-90%, more preferably 90-95%, and most preferably 98-100% sequence identity to the reference sequence over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

Additionally, as defined herein, a nucleotide sequence is intended to refer to a natural or synthetic linear and sequential array of nucleotides and/or nucleosides, and derivatives thereof. The terms "encoding" and "coding" refer to the process by which a nucleotide sequence, through the mechanisms of transcription and translation, provides the information to a cell from which a series of amino acids can be assembled into a specific amino acid sequence to produce a polypeptide.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized, as shown below in Table 1. General information and reviews of AAV can be found in, for example, Carter, 1989, *Handbook of Parvoviruses*, Vol. 1, pp. 169-228, and Berns, 1990, *Virology*, pp. 1743-1764, Raven Press, (New York). The type 6 and type 2 AAV serotypes have been used to illustrate the present invention in the Examples provided herein below. However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of *Parvoviruses and Human Disease*, J. R. Pattison, ed.; and Rose, *Comprehensive Virology* 3:1-61 (1974)). For example, all AAV serotypes apparently exhibit very similar replication properties mediated by homologous rep genes; and all bear three related capsid proteins such as those expressed in AAV 6. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products, i.e., AAV Rep and Cap proteins, and wherein the host cell has been transfected with a vector which encodes and expresses a protein from the adenovirus open reading frame E4orf6. When an AAV vector is incorporated into a larger polynucleotide, e.g., in a chromosome or in another vector such as a plasmid used for cloning or transfection, then the AAV vector is typically referred to as a "pro-vector". The pro-vector can be "rescued" by replication and encapsidation in the presence of AAV packaging functions and necessary helper functions provided by E4orf6.

An "AAV virion" or "AAV viral particle" or "AAV vector particle" refers to a viral particle composed of at least one AAV capsid protein (preferably by all of the capsid proteins of a particular AAV serotype) and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

"Packaging" as used herein refers to a series of subcellular events that results in the assembly and encapsidation of a viral vector, particularly an AAV vector. Thus, when a suitable vector is introduced into a packaging cell under appropriate conditions it can be assembled into a viral particle. Functions associated with packaging of viral vectors, particularly AAV, are described herein and in the art.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap gene in accordance with the present invention encodes a Cap protein which is capable of packaging AAV vectors in the presence of rep and adeno helper function and is capable of binding target cellular receptors. In some embodiments, the AAV cap gene encodes a capsid protein having an amino acid sequence derived from a particular AAV serotype, for example the serotypes shown in Table 1. In some embodiments, the AAV cap gene encodes a hybrid capsid protein comprising an amino acid sequence comprising a first region that is derived from a first AAV serotype and at least a second region that is derived from a second AAV serotype. In some embodiments, the AAV cap gene encodes a capsid protein variant, having at least 70%, (such as at least 80%, at least 85%, at least 90%, at least 95% or at least 98% identity with the nucleotide sequence encoding the cap ORF in its respective AAV serotype.

As used herein, the terms "host cells," "cell lines," "cell culture," "packaging cells," and other such terms describe higher eukaryotic cells, preferably mammalian cells, most preferably human cells, useful in the present invention. These cells can be used as recipients for recombinant vectors, viruses or other transfer polynucleotides, and include the progeny of the original cell that was transduced. It is understood that the progeny of a single cell may not necessarily be completely identical, in, for example, morphology or in genomic complement, to the original parental cell.

As described herein, the inventors have determined that a correlation exists between the presence of cap gene contaminants in packaged AAV vector preparations and the immunogenicity of such AAV vectors when administered to a mammalian subject. As described in Example 1, the inventors discovered that AAV capsids can package DNA that does not contain AAV ITR sequences, and show that the packaged DNA can express protein in vector-transduced cells. As described in Example 2, consistent with the results observed in Example 1, the inventors were able to detect cap and rep DNA in several AAV vectors made using standard techniques (i.e., cap expression vectors not modified with a heterologous intron) and found expression of Cap proteins in cells transduced with standard AAV vector preparations by using a sensitive complementation assay.

Accordingly, the present invention provides compositions comprising an intron-modified cap expression cassette, wherein the expression cassette is at least 5 kilobases in length (cap+intron, also referred to as "captron") and methods of using the same for generating adeno-associated virus (AAV) vector particles with reduced or undetectable levels of cap gene contamination. As described in Example 3, the inventors generated a novel intron-modified cap expression cassette (captron construct) which eliminates capsid gene transfer and capsid expression in transduced cells. As described in Example 4, the inventors demonstrated that AAV vectors generated using the captron construct are dramatically less immunogenic when administered to a dog at therapeutic in vivo amounts than AAV vectors generated using the standard cap6 construct that is not modified with a heterologous intron. In view of the results demonstrated herein, it is expected that AAV vectors produced using captron plasmids will generate an increase in the number of transduced cells and in vivo persistence of a therapeutic transgene of interest. It is also expected that AAV-captron generated vectors will reduce the level of, or eliminate the need for, an immunosuppressive regimen after AAV vector transduction in a mammalian subject.

In accordance with the foregoing, in one aspect, the invention provides an intron-modified cap expression cassette (captron) useful for generating adeno-associated virus (AAV) vector particles. The intron-modified cap expression cassette in accordance with this aspect of the invention comprises: (i) a nucleic acid molecule comprising a nucleotide sequence encoding AAV capsid protein operably linked to a promoter, wherein the encoded AAV capsid protein is capable of packaging AAV vectors in the presence of rep and adeno helper functions, and (ii) at least one heterologous intron sequence operably linked to the nucleotide sequence encoding the AAV capsid protein; wherein the total length of the expression cassette is at least 5 kilobases.

Figure 2A:
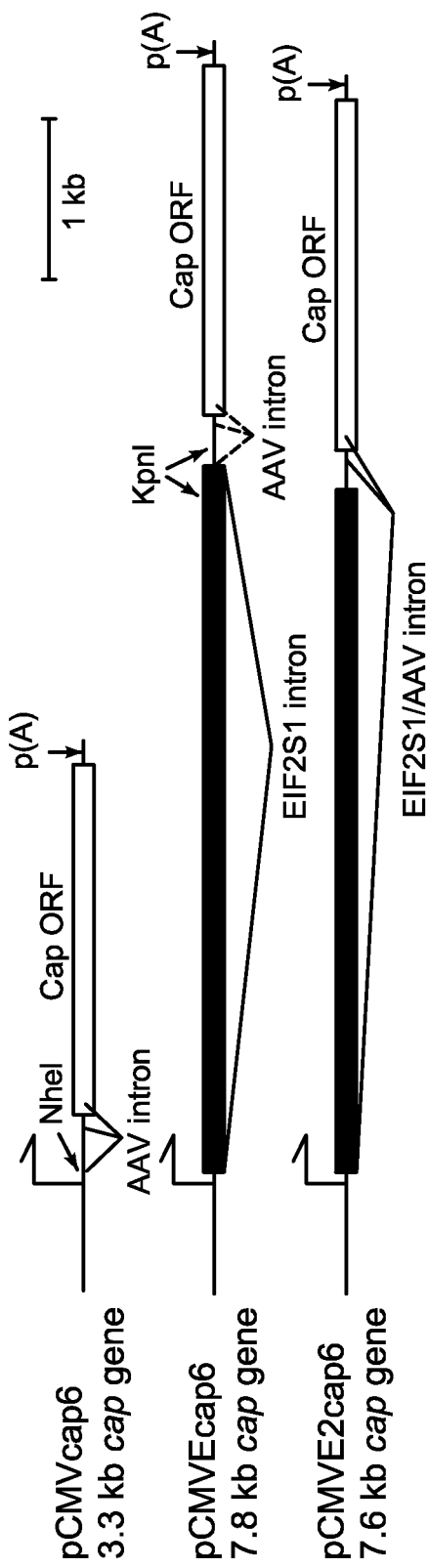
FIG. 2A illustrates representative expression cassettes comprising a nucleotide sequence encoding the cap6 ORF with and without a heterologous intron inserted upstream of the cap open reading frame, as described in Example 3.

FIGS. 2A (pCMVE2cap6) and 2C illustrate exemplary embodiments of an intron-modified cap expression cassette (10) in accordance with this aspect of the invention. As shown in FIG. 2C, the expression cassette (10) includes a nucleotide sequence encoding an AAV capsid protein (cap open reading frame (ORF)) (40), operably linked to a promoter (20), and at least one heterologous intron sequence (30) operably linked to the nucleotide sequence encoding the AAV Cap protein (40).

In accordance with this aspect of the invention, the expression cassette 10 includes a nucleotide sequence encoding an AAV capsid protein that is capable of packaging AAV vectors in the presence of rep and adeno helper functions. The expression cassette 10 may include a nucleotide sequence encoding a cap ORF from any AAV serotype, including AAV serotypes that are human or non-human. At least 13 AAV serotypes have been identified, cloned and sequenced, and at least 100 new AAV variants have been isolated from non-primates, primates and humans. Exemplary serotypes are described in TABLE 1 and include Serotypes AAV-1, AAV-2, AAV-3, AAV-4, AAV-5, AAV-6, AAV-7, AAV-8, AAV-9, AAV-10, AAV-11, AAV-12 and AAV-13. In a particularly preferred embodiment, the present invention provides an expression cassette comprising a nucleotide sequence encoding AAV type 2 cap ORF (SEQ ID NO:8), or AAV type 6 cap ORF (SEQ ID NO:1).

In some embodiments, the expression cassette comprises a nucleotide sequence encoding a cap ORF variant sequence, the variant sequence having at least 70% sequence identity, more preferably at least about 80%, more preferably at least 85%, at least 90%, at least 95% or at least 98% sequence identity with the nucleotide sequence encoding the Cap ORF in its respective AAV serotype. In one embodiment, the expression cassette comprises a nucleotide sequence encoding a cap ORF variant sequence having at least 70% sequence identity, more preferably at least about 80%, more preferably at least 85%, at least 90%, at least 95% or at least 98% sequence identity with the nucleotide sequence encoding the Cap ORF from AAV serotype 2 (SEQ ID NO:8) or AAV serotype 6 (SEQ ID NO:1).

In some embodiments, the expression cassette comprises a nucleotide sequence encoding a cap ORF variant sequence with regions or domains or individual amino acids that are derived from two or more different serotypes (also referred to as a chimeric or hybrid AAV capsid), wherein the cap ORF variant sequence is capable of packaging AAV vectors in the presence of rep and adeno helper function and is capable of binding target cellular receptors. Exemplary chimeric AAV variant capsid sequences suitable for use in the present invention are described in U.S. Patent Publication No. 2010/0047174, hereby incorporated herein by reference. As described in U.S. Patent Publication No. 2010/0047174, an alignment of the amino acid sequences of various capsid proteins shows conservation of the five known loops on the exterior of the AAV capsid which are likely to be involved in capsid binding to cellular receptors and recognized by neutralizing antibodies. Accordingly, in a preferred embodiment the cap ORF variant sequence for use in the present invention comprises the five known loop regions derived from one or more different serotypes, and is capable of binding to cellular receptors.

It has been demonstrated that AAV vectors can be replicated and packaged into infectious viral particles when present in a host cell that has been transfected with a vector encoding and expressing rep and cap gene products, i.e., AAV Rep and Cap proteins, and wherein the host cell has been transfected with a vector which encodes and expresses a protein from the adenovirus open reading frame E4orf6. It has been further demonstrated that rep and cap transcription units may be provided as two separate plasmids relative to single AAV packaging plasmids. Presentation on separate plasmids apparently improves the function of the heterologous promoters to initiate transcription of the associated polynucleotide. See, e.g., U.S. Pat. Nos. 7,208,315 and 6,541,258, each hereby incorporated herein by reference. For example, as described in U.S. Pat. No. 6,541,258, an AAV "split-cap" packaging system is described which utilizes a recombinant gene encoding one or more AAV Cap proteins, which gene is separated from rep-specific sequences of an AAV rep gene, i.e., rep78. The split-cap gene is operably linked to a promoter, preferably a heterologous promoter, i.e., a promoter other than the AAV P40 promoter, which heterologous promoter is incorporated upstream of the split-cap coding region, either in place of or in addition to the P40 promoter.

Although the split packaging system (e.g., using a plasmid called "CMV-cap" as described in U.S. Pat. No. 6,541,258, and illustrated in FIG. 2A), is capable of generating high titer AAV vector particles, as demonstrated in Example 2 herein, cap and rep DNA contamination was observed in preparations of AAV vector particles made using the CMV-cap construct (i.e., a cap expression vector not modified with a heterologous intron). As further described in Example 2, expression of Cap proteins was observed in cells transduced with standard AAV vector preparations by using a sensitive complementation assay. It is noted that traditional methods of AAV vector preparation typically utilize capsid expression cassettes that are small enough to be packaged within the AAV virion. Many copies of the cap plasmid are present within the cell following transfection, increasing the possibility for packaging. Alternative methods using cell lines with integrated copies of the rep and cap genes would most likely not circumvent this problem, as it has been shown that efficient expression of AAV from cell lines required amplification of the rep and cap genes out of their integrated form.

The expression cassette (10) of the present invention was designed to avoid cap gene packaging in AAV vector preparations, by introducing a heterologous intron sequence (30) into a cap expression cassette (10), wherein the heterologous intron sequence (30) is large enough to increase the total size of the expression cassette (10) to more than 5 kilobases.

It is known that the packaging size limit of AAV vectors is limited to the size of the parent wild-type AAV genome, which ranges in size based on the AAV serotype (i.e., from 4,087 to 4,767). See, e.g., Wu Z. et al., *Mol Ther* 18(1):80-86 (2010). For example, wild-type AAV-2 has a genome size of 4,679, and wild-type AAV-6 has a genome size of 4,683 (see TABLE 1). Therefore, in order to avoid packaging, the total size of the intron-modified expression cassette is at least 5 kilobases (kb), such as at least 5.2 kb, such as at least 5.5 kb, such as at least 6 kb, such as at least 6.5 kb, such as at least 7 kb, such as at least 7.5 kb, such as at least 8 kb, such as at least 9 kb, such as at least 10 kb, such as at least 50 kb, such as at least 100 kb or longer.

The heterologous intron sequence (30) included in the expression cassette (10) may comprise any heterologous intron sequence, provided that the heterologous intron sequence is operably linked to the transcriptional unit encoding the cap ORF (i.e., the expression cassette comprising the heterologous intron contains at least one splice donor and splice acceptor sites allowing for proper splicing of the transcription unit encoding the cap ORF). In accordance with this aspect of the invention, the total length of the intron-modified expression cassette (10) is at least 5 kb to avoid being packaged into AAV vector particles. Accordingly, the heterologous intron sequence (30) is chosen such that it comprises a sufficient length to bring the total size of the expression cassette (10) to a length of at least 5 kb. For example, as shown in FIG. 2C, a representative embodiment of the expression cassette (10) comprising the AAV6 Cap ORF referred to as "pCMVE2Cap6", the total combined size of the promoter (20), Cap6 ORF (40), and polyA (50) is approximately 3.2 kb, therefore, the size of the heterologous intron (30) suitable for insertion in this exemplary expression cassette (10) would be at least 1.8 kb, in order to result in an expression cassette (10) having a total length of at least 5 kb.

In some embodiments, the expression cassette comprises multiple heterologous introns, wherein at least one of the heterologous introns is operably linked to the cap ORF, and wherein the multiple heterologous introns are chosen such that the combined size of the heterologous introns brings the total size of the expression cassette to at least 5 kb.

Accordingly, in some embodiments, the at least one heterologous intron sequence, or the combined size of multiple heterologous intron sequences, is at least 1.8 kb, such as at least 2.0 kb, such as at least 2.5 kb, such as at least 3.0 kb, such as at least 3.5 kb, such as at least 4.0 kb, such as at least 4.5 kb, such as at least 5.0 kb, such as at least 6.0, such as at least 1 kb, such as at least 5 kb or longer.

In some embodiments, the heterologous intron (30) comprises at least one splice donor and one or more splice acceptor sites to allow for the proper splicing of the transcription unit encoding the cap ORF (40), resulting in VP1, VP2, and VP3. A heterologous intron sequence can contain, or be modified to contain, appropriate splice donor and splice acceptor sites for the proper slicing of the transcription unit encoding the cap ORF based on the knowledge in the art regarding the wild type AAV genome. As known by those of skill in the art, the right side of a positive sense single strand wild type AAV genome encodes overlapping sequences of three capsid proteins, VP1, VP2 and VP3, which start from one promoter, designated p40. The molecular weights of these VP proteins are 87, 72 and 6 kiloDaltons, respectively (Jay, F. T., et al., *Proc. Natl. Acad. Sci.* 78:2927-31 (1981)). All three capsid proteins are translated from one mRNA. After this mRNA is synthesized, it can be spliced in two different manners: either a longer or shorter endogenous AAV intron can be excised, resulting in the formation of two pools of mRNAs: a 2.3 kb and a 2.6 kb long mRNA pool. Usually, and especially in the presence of adenovirus, the longer intron is preferred, so the 2.3 kb long mRNA represents the "major splice." In this form, the first AUG codon, from which the synthesis of VP1 protein starts, is cut out, resulting in a reduced overall level of VP1 protein synthesis. The first AUG codon that remains in the major splice is the initiation codon for VP3 protein. However, upstream of that codon in the same open reading frame (ORF) is an ACG sequence (threonine) which is surrounded by an optimal Kozak sequence, which contributes to a low level of synthesis of VP2 protein, which includes the amino acids of VP3 protein with additional N terminal residues. Jay, F. T., et al., *Proc. Natl. Acad. Sci.* 78:2927-31 (1981); Cassinotti, P., et al., Virology 167:176-84 (1988); Trempe, J. P., et al., *J. Virology* 62(9):3356-63 (1988).

In another embodiment, as illustrated in FIG. 2C, the heterologous intron (30) in the expression cassette (10) comprises a hybrid sequence with a first region (36) comprising a heterologous intron sequence and a second region (38) comprising at least a portion of an AAV intron sequence (e.g., SEQ ID NO:3 which comprises a portion of the AAV-6 intron containing $SA_1$, $SA_2$). In accordance with such embodiments, the second regio (38) comprising at least a portion of an AAV intron sequence may be from the same, or a different AAV serotype then the serotype of the cap ORF. The representative expression cassette shown in FIG. 2C comprises AAV-6 Cap ORF (SEQ ID NO:1, encoding AAV-6 capsid protein, set forth as SEQ ID NO:2), and includes an hybrid intron (30) located between the CMVp and the cap ORF, wherein the hybrid intron comprises a first region (36) comprising an intron sequence from the heterologous gene EIF2S1 (SEQ ID NO:5), which contains a splice donor (SD) sequence, and a second region (38) comprising at least a portion of the endogenous AAV-6 intron (SEQ ID NO:4), which comprises a subregion (SEQ ID NO:3) containing the first endogenous splice acceptor site ($SA_1$) and the second endogenous splice acceptor site ($SA_2$) from AAV-6.

The heterologous intron (30) may be positioned in any suitable location within the expression cassette (10) provided that the intron is operably linked to the cap ORF (40) to allow for appropriate expression of the capsid proteins (VP1, VP2 and VP3). For example, the heterologous intron (30) may be positioned within the cap coding region, or between the promoter and the cap coding region, or in the 3' untranslated region. In one embodiment, as illustrated in FIG. 2C, the heterologous intron (30) is positioned between the promoter (20) and the cap ORF (40).

The intron-modified cap expression cassette (10) as described herein may be generated using standard molecular biology techniques and can be assessed for the ability to produce Cap proteins VP1, VP2 and VP3 using Western blot analysis, as described in Example 3. The expression cassette (10) can be further assessed for the ability to produce Cap proteins capable of packaging AAV vector particles using the methods described in Example 3.

The promoter (20) for use in the expression cassette which is operably linked to the AAV cap ORF may be the promoter naturally associated with the AAV cap gene (i.e., p40), or may be a heterologous (non-AAV) promoter. Preferably, a strong promoter such as a cytomegalovirus (CMV) promoter, particularly the CMV major IE gene promoter, is used to express the AAV cap gene. Other examples of suitable strong promoters include, but are not limited to, the retroviral Rous sarcoma virus (RSV) LTR promoter, SV40 promoter, the dihydrofolate reductase promoter, the beta-actin promoter, the phosphoglycerol kinase (PGK) promoter, and the EF1 promoter.

As illustrated in FIG. 2C, in one embodiment, the expression cassette (10) comprises a promoter (20), an intron (30) comprising heterologous (non-AAV) sequences operably linked to the cap ORF (40), and a polyadenylation sequence (50). In one embodiment, the expression cassette (10) is provided in the form of pCMVE2Cap6 (SEQ ID NO:7). As illustrated in FIG. 2C, the pCMVE2Cap6 construct contains an expression cassette comprising the cap ORF (40) driven by the CMVp (20) and an intron (30) comprising non-AAV sequences, wherein the total size of the expression cassette (10) is at least 5 kb to prevent packaging of the nucleic acid sequence encoding AAV Cap protein in the AAV vector particles. The representative expression cassette shown in FIG. 2C, the AAV cap ORF (40) comprises AAV-6 Cap ORF (SEQ ID NO:1), and includes a hybrid intron (30) located between the CMVp and the cap ORF, wherein the hybrid intron comprises a first region (36) comprising an intron from the heterologous gene EIF2S1 (SEQ ID NO:5) containing a splice donor sequence, and a second region (38) comprising at least a portion of the endogenous AAV-6 intron (SEQ ID NO:4) which comprises a subregion (SEQ ID NO:3) containing the first endogenous splice acceptor site ($SA_1$) and the second endogenous splice acceptor site ($SA_2$) from AAV-6.

While the invention is described in connection with the representative AAV-6 cap ORF and intron sequences, it is contemplated that the compositions and methods may include sequences corresponding to the Cap ORF (e.g., SEQ ID NO:1, encoding SEQ ID NO:72) from AAV-6 and the intron region corresponding to the AAV-6 intron (SEQ ID NO:4), or at least a subregion thereof containing the $SA_1$ and $SA_2$ splice acceptor sites corresponding to the AAV-6 subregion (SEQ ID NO:3) obtained from other known AAV serotypes, such as, for example, the Cap ORF from AAV-2 (SEQ ID NO:8, encoding the AAV-2 capsid protein, set forth as SEQ ID NO:9). Capsid proteins suitable for use in the expression cassettes and methods of the invention include capsid proteins from AAV serotypes that are human or non-human. Representative AAV serotypes that may be included in the compositions and methods of the invention are provided in TABLE 1, and include Serotypes AAV-1, AAV-2, AAV-3, AAV-4, AAV-5, AAV-6, AAV-7, AAV-8, AAV-9, AAV-10, AAV-11, AAV-12 and AAV-13.

TABLE 1

AAV Serotypes for Use in the Compositions and Methods

| AAV Serotype | Genome Size | GenBank Ref Number (NCBI accessed Aug. 11, 2010), wherein each sequence listed below is hereby incorporated by reference. |
| --- | --- | --- |
| AAV-1 | 4,718 bp linear genomic | NC_002077.1 |
| AAV-2 | 4,679 bp linear genomic | NC_001401.2 |
| AAV-3 | 4,726 bp linear genomic | NC_001729.1 |
| AAV-3B | 4,722 bp linear genomic | AF028705.1 |
| AAV-4 | 4,767 bp circular genomic | NC_001829.1 |
| AAV-5 | 4,642 bp linear genomic | NC_006152.1 |
| AAV-6 | 4,683 bp linear genomic | AF028704.1 |
| AAV-7 | 4,721 bp linear genomic | NC_006260.1 |
| AAV-8 | 4,393 bp linear genomic | NC_006261.1 |
| AAV-9 | 4,385 bp linear genomic | AX753250.1 |
| AAV-10 | 4,102 bp linear genomic | AY631965.1 |
| AAV-11 | 4,087 bp linear genomic | AY631966.1 |
| AAV-12 | 4,213 bp linear genomic | DQ813647.1 |
| AAV-13 | 4,180 bp linear genomic | EU285562.1 |

In other embodiments, the expression cassette (10) may optionally include sequences encoding the AAV Rep 78/68 proteins and/or adenoviral helper functions (e.g., the adenoviral proteins E1, E2a, and E4 ORF6).

In some embodiments, the expression cassette (10) is included in a genetic element, such as a vector, which may be delivered to a host cell, e.g., naked DNA, a plasmid, phage, transposon, cosmid, episome, a protein in a non-viral delivery vehicle (e.g., a lipid-based carrier), virus, etc., which transfers the sequences carried thereon. The selected vector may be delivered by any suitable method, including transfection, electroporation, liposome delivery, membrane fusion techniques, high velocity DNA-coated pellets, viral infection and protoplast fusion. In some embodiments, the expression cassette (10) is included in a vector, such as a plasmid, along with an origin of replication which allows for replication of the plasmid in an appropriate host cell. In some embodiments, the expression cassette (10) is included in a vector, such as a plasmid comprising nucleic acid sequences allowing for selection in a suitable host (e.g., sequences that encode a phenotypic marker or reporter gene detectable by a suitable assay). In some embodiments, the expression cassette (10) is present in a host cell, either as an episome or stably integrated into the genome of the host cell.

In some embodiments, the intron-modified cap expression cassette is contained in a vector that optionally includes sequences encoding the AAV Rep 78/68 proteins and/or adenoviral helper functions (e.g., the adenoviral proteins E1, E2a, and E4 ORF6). In some embodiments, the intron-modified cap expression cassette is contained in a vector that does not contain an AAV rep gene. In some embodiments, the intron-modified cap expression cassette is contained in a vector that contains the AAV rep gene in a separate transcriptional unit and optionally also contains the adenoviral proteins E1, E2a, and E4 ORF6.

In another aspect, the invention provides a method of reducing cap gene contamination in AAV vector particles. The method comprises: (a) introducing an AAV vector into a suitable host cell comprising an intron-modified cap expression cassette as described herein; (b) expressing rep and adeno helper functions in the host cell; and (c) culturing the host cell to produce AAV vector particles.

The intron-modified cap expression cassette may be introduced into a host cell using standard DNA transfection techniques. See, e.g., Sambrook et al., *Molecular Cloning: A Laboratory Manual*, 3d Ed., Cold Spring Harbor Press, Plainview, N.Y. (2000).

The transforming DNA may or may not be integrated into the genome of the host cell. In one embodiment, the host cell is a mammalian packaging cell which also comprises rep and adeno helper functions sufficient for generating infectious AAV vector particles. In some embodiments, the host cell further comprises an AAV vector. As described herein, when a suitable AAV vector is introduced into a packaging cell, such as a cell comprising an intro-modified cap expression construct as described herein, the AAV vector can be assembled into a viral particle with reduced or no cap gene contamination.

In accordance with this aspect of the invention, the production of AAV vectors comprises the preparation of mammalian packaging cells that comprise an intron-modified cap expression cassette, a polynucleotide encoding an AAV rep gene and adenovirus helper functions (e.g., a polynucleotide encoding an adenovirus E4orf6 gene). In some embodiments, the AAV rep gene and the intron-modified cap expression cassette are provided on a single vector. In other embodiments, the rep and cap genes are provided on separate vectors. The packaging cells are then infected or transfected with a plasmid comprising the AAV inverted terminal repeat regions positioned on either side of a polynucleotide encoding a gene of interest. Under suitable conditions expression of the rep, cap, and E4orf6 genes of the packaging cell results in the synthesis of the Rep, Cap, and E4orf6 proteins which mediate replication and encapsidation of the AAV vector. Providing a polynucleotide which encodes a gene of interest between the AAV ITR sequences of the AAV vector results in packaging of the polynucleotide of interest into an infectious AAV vector particle which can be used to deliver the gene of interest to a desired host cell.

In some embodiments, the AAV vector particles generated in accordance with the methods of this aspect of the invention comprise a nucleic acid sequence encoding a heterologous (non-AAV) gene, such as a therapeutic gene. Typically, in the context of the present invention, such heterologous genes are located within the AAV vector, which vector is flanked by terminal repeat (ITR) regions and therefore can be replicated and encapsidated into AAV vector particles. Target heterologous genes can be used in this invention to generate AAV vectors for a number of different applications. Such heterologous genes include, but are not limited to, (i) polynucleotides encoding proteins useful in other forms of gene therapy to relieve deficiencies caused by missing, defective or sub-optimal levels of a structural protein or enzyme; (ii) polynucleotides that are transcribed into antisense molecules; (iii) polynucleotides that are transcribed into decoys that bind transcription or translation factors; (iv) polynucleotides that encode cellular modulators, such as cytokines; (v) polynucleotides that can make recipient cells susceptible to specific drugs, such as the herpes virus thymidine kinase gene, and the like; and (vi) polynucleotides for the treatment of various cancers.

Methods of culturing packaging cells and exemplary conditions which promote the release of AAV vector particles, such as the producing of a cell lysate, may be carried out as described in Examples 1-4 herein. Producer cells are grown for a suitable period of time in order to promote release of virus into the media. Generally, cells may be grown for about 24 hours, about 36 hours, about 48 hours, about 72 hours, about 4 days, about 5 days, about 6 days, about 7 days, about 8 days, about 9 days, up to about 10 days. After about 10 days (or sooner, depending on the culture conditions and the particular producer cell used), the level of production generally decreases significantly. Generally, time of culture is measured from the point of viral production. For example, in the case of AAV, viral production generally begins upon supplying helper virus function in an appropriate producer cell as described herein. Generally, cells are harvested about 48 to about 100, preferably about 48 to about 96, preferably about 72 to about 96, preferably about 68 to about 72 hours after helper virus infection (or after viral production begins).

In some embodiments, the methods further comprise purification steps, such as treatment of the cell lysate with benzonase, purification of the cell lysate over a CsCl gradient, or purification of the cell lysate with the use of heparin sulphate chromatography, as described in Halbert C. L. and Miller, A. D., *Methods Mol. Biol.* 246:201-212 (2004), hereby incorporated herein by reference.

The AAV vector particles produced using the captron plasmid have a reduced amount or an undetectable amount of cap gene as compared to AAV vector particles generated using standard cap6 packaging plasmids (non-intron modified), as described in Examples 2-4 herein. The presence or amount of cap DNA contamination in a preparation of AAV vector particles can be determined using quantitative PCR analysis, for example, as described in Example 2, and/or the presence or amount of cap gene contamination in a preparation of AAV vector particles can be determined by a complementation assay, as described in Example 3.

In another aspect, the present invention provides a method of reducing the immune response in a mammalian subject undergoing treatment with an AAV vector comprising administering to the mammalian subject a preparation of AAV vector particles comprising a nucleic acid sequence encoding a therapeutic molecule, wherein the preparation of AAV vector particles was produced with an intron-modified cap expression cassette, wherein the immune response in the mammalian subject exposed to an AAV vector generated using the intron-modified cap expression cassette is significantly reduced or absent as compared to the immune response generated with a preparation of AAV vector particles generated using a standard cap expression cassette.

The AAV vector particles for use in the methods of this aspect of the invention, generated using the intron-modified cap expression cassette as described herein, avoid the generation of an immune response to the AAV capsid sequences in a mammalian subject, as demonstrated in Example 4 herein. The AAV vector particles are administered to a mammalian subject in sufficient amounts to provide sufficient levels of gene transfer and expression to provide a therapeutic benefit without undue adverse effects, such as an immune response. In some embodiments, the use of the AAV vector particles generated using the intron-modified cap expression cassette obviates the need for treatment of the subject with immunosuppressive drugs, as described in Example 4, due to the reduction or absence of immune response in the subject to the AAV vector treatment.

The AAV vector particles may be administered to a mammalian subject using conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intracochlear, intravenous, intramuscular, subcutaneous, intradermal, and other parental routes of administration. Routes of administration may be combined, if desired.

Dosages of the AAV vector particles will depend primarily on factors such as the condition being treated, the age, weight and health of the patient, and may thus vary among patients. For example, a therapeutically effective human dosage of the AAV vector particles is generally in the range of from about 0.1 mL to about 100 mL of solution containing concentrations of from about $10^9$ to $10^{16}$ genomes of the virus vector. A preferred human dosage for delivery to large organs (e.g., liver, muscle, heart and lung) may be about $5 \times 10^{10}$ to $5 \times 10^{13}$ AAV genomes per 1 kg, at a volume of about 1 to 100 mL. A preferred dosage for delivery to eye or ear (cochlea) is about $5 \times 10^9$ to $5 \times 10^{12}$ genome copies, at a volume of about 0.1 mL to 1 mL. The dosage will be adjusted to balance the therapeutic benefit against any side effects and such dosages may vary depending upon the therapeutic application for which the vector is employed. The levels of expression of the transgene can be monitored to determine the frequency of dosage resulting in viral vectors.

In another aspect, the present invention provides a complementation assay for measuring the presence or amount of cap or rep gene contamination in a preparation of recombinant AAV vector virions.

In one embodiment, the complementation assay is carried out to measure the presence or amount of cap gene contamination in a preparation of AAV vector virions and comprises (a) infecting a host cell with a test preparation of AAV vector, wherein the host cell comprises: (i) an indicator AAV vector with a detectable marker, (ii) a rep expression vector; and (iii) adenovirus helper functions; (b) culturing the host cell for a period of time sufficient to generate AAV vector virions from the indicator AAV vector; (c) contacting an indicator cell with cell lysate obtained from the host cells cultured in accordance with step (b); and (d) determining the presence or amount of indicator cells that are positive for the detectable marker, wherein a positive result indicates that the test preparation of AAV vector virions contains cap gene contamination.

In another embodiment, the complementation assay is carried out to measure the presence or amount of rep gene contamination in a preparation of AAV vector virions and comprises (a) infecting a host cell with a test preparation of AAV vector, wherein the host cell comprises: (i) an indicator AAV vector with a detectable marker, (ii) a cap expression vector, and (iii) adenovirus helper functions; (b) culturing the host cell for a period of time sufficient to generate AAV vector virions from the indicator AAV vector; (c) contacting an indicator cell with a cell lysate obtained from the host cells cultured in accordance with step (b); and (d) determining the presence or amount of indicator cells that are positive for the detectable marker, wherein a positive result indicates that the test preparation of AAV vector virions contains rep gene contamination.

FIG. 1 provides a flow diagram illustrating a representative, non-limiting embodiment in accordance with this aspect of the invention.

In some embodiments, the complementation assay further comprises treating the test preparation of AAV vector and/or the cell lysate obtained from the host cells with benzonase, for example, as shown in FIG. 1 and described in Example 3.

Indicator AAV vectors for use in the complementation assay comprise at least one detectable or selectable marker(s). Suitable markers include genes which confer antibiotic resistance or sensitivity, or impart color, or change the antigenic characteristics when cells which have been transduced with the AAV vector particles are grown in an appropriate selective medium. Particular selectable marker genes useful in the practice of the invention include the Alkaline phosphatase gene, Green fluorescent protein (GFP), Neomycin resistance gene (encoding Neomycin phosphotransferase) that allows selection in mammalian cells by conferring resistance to G418 (available from Sigma, St. Louis, Mo.) and the Hygromycin-B resistance gene (encoding Hygromycin-B-phosphotransferase) that confers resistance to Hygromycin-B. Other suitable markers are known to those of skill in the art.

The following examples merely illustrate the best mode now contemplated for practicing the invention, but should not be construed to limit the invention.

Example 1

This Example demonstrates that genes without flanking AAV ITRs, such as those present in packaging constructs used for expression of Cap and Rep during AAV vector production, can be packaged into AAV vectors and expressed in cells transduced with the AAV vectors.

Rationale:

In several clinical trials using AAV vector transduction in human subjects, an immune response to capsid has been detected. For example, in a clinical trial for hemophilia B, two of seven subjects given an AAV vector-expressing clotting factor IX (FIX) developed a transient self-limiting increase in liver transaminases, followed by clearance of the FIX-expressing cells at 4 to 8 weeks after delivery (Manno, C. S., et al., *Nat. Med.* 12:342-347 (2006)). In this clinical trial for hemophilia B, a cytotoxic lymphocyte (CTL) response to AAV capsid but not to FIX was detected in peripheral blood mononuclear cells. In another clinical trial involving lipoprotein lipase, clearance of AAV vector-transduced cells coincided with a CTL response towards the capsid, but not the transgene (Mingozzi, F., et al., *Blood* 114:2077-2086 (2009)). It is important to know how this immune response to AAV capsid is generated in order to prevent it. One hypothesis suggests that persistence of Cap proteins from the vector inoculum results in clearance of the transduced cells. An alternative hypothesis suggests that the immune response results from Cap expression that occurs in the transduced cells due to cap gene transfer by AAV vectors. A clinical protocol that uses transient immunosuppression may be successful if the former hypothesis is true, but if the later hypothesis is true, an immune response is likely to occur when immunosuppression is lifted. It is also possible that both mechanisms occur, and in this case, successful long-term transduction by AAV vectors will require both transient immunosuppression and methods to prevent AAV vector contamination with capsid-expressing DNA. The observation of a capsid-directed immune response even after 16 weeks of immunosuppression in a canine model of muscle gene transfer suggests a stable source of antigen (Wang, Z., et al., *Mol. Ther.* 15:1160-1166 (2007)). We also have observed an immune response to AAV6 capsid that significantly decreased transgene expression within 3 weeks after transduction in a canine model of lung gene transfer (Halbert, C. L., et al., *Mol. Ther.* 18:1165-1172 (2010)). In this canine model, immune suppression promoted long term gene expression (4 months) but that was lost after immune suppression was lifted. Id. Assuming that the capsid protein associated with vector virions had disappeared by this time, the delayed immune response suggests a continuous source of capsid expression, perhaps due to transfer of cap genes by the vector preparation.

The development of AAV vectors for clinical use is marked by continuing efforts to improve efficiency and to remove impurities. Early methods of AAV vector production resulted in contamination with replication-competent AAV. While several strategies were used to prevent such contamination (see, e.g., Allen, J. M., et al., Debelak, D. J., Reynolds, T. C., and Miller, A. D., *J. Virol.* 71:6816-6822 (1997); Cao, L., et al., *J. Virol.* 74:11456-11463 (2000); and Nony, P., et al., *J. Virol.* 77:776-781 (2003)), packaging of other DNA sequences into AAV virions can still occur. For example, DNA encoding the bacterial ampicillin resistance gene originating from plasmids used to make AAV vectors has been found in AAV vector preparations at 0.5-7% of the level of vector genomes (vg) (Chadeuf, G., et al., *Mol. Ther.* 12:744-753 (2005)). DNA encoding the ampicillin resistance gene was also found in tissues of mice, dogs, and non-human primates up to 5 months after AAV vector delivery, demonstrating that DNA impurities in AAV vector preparations can persist in vivo. Id. Furthermore, the presence of cap DNA sequences in clinical lots of AAV vectors at a level of 0.00018 cap DNA copies per vg has been reported by Hauck B., et al., *Mol. Ther.* 17:144-152 (2009)). However, Hauck et al. did not detect capsid expression in recipient mice or cultured cells, as measured by quantitative PCR (qPCR) of reverse-transcribed mRNA obtained from the cultured cells.

This Example describes an experiment that was carried out to determine whether the immune response to Cap observed in the various clinical trials and animal models results from Cap expression that occurs in the transduced cells due to cap gene packaged in AAV vectors. This Example describes a comparison of the rate of AAV-mediated transduction of a gene that encodes human placental alkaline phosphatase (AP), either flanked by ITRs in the standard AAV vector configuration (designated pARAP4), or without any flanking AAV sequences (pRAP).

Methods:

Cell Culture:

Human embryonic kidney (HEK) 293 cells (ATCC CRL 1573) and HTX cells, an approximately diploid subclone of human HT-1080 fibrosarcoma cells (ATCC CCL 121), were maintained in Dulbecco's modified Eagle medium (DMEM) supplemented with 10% Cosmic Calf serum (Thermo Scientific) or 10% fetal bovine serum (FBS), respectively.

AAV Vector Plasmids.

ARAP4 is an AAV2-based vector (Allen, J. M., et al., *Mol. Ther.* 1:88-95 (2000)) which expresses Alkaline phosphatase (AP) and contains the RSV promoter/enhancers, the AP cDNA, and SV40 polyadenylation sequences, flanked by AAV2 ITRs.

The plasmid pRAP was generated by deleting the AAV2 ITRs from pARAP4.

The ACWRZn and ACZn vectors express a nuclear-localized βgal protein flanked by AAV ITRs (Halbert, C. L., et al., *Hum. Gene Ther.* 18:344-354 (2007)).

The ACAGhAAT vector expresses human α1-antitrypsin (Halbert, C. L., et al., *Mol. Ther.* 18:1165-1172 (2010)).

The ACF3'B vector was derived from ARAP4 and contains the 3' portion of the human CFTR cDNA (2.1 kb region downstream of the HpaI site).

The ACMVcFIX vector expresses canine clotting factor FIX and was kindly provided by Katherine High (Children's Hospital of Philadelphia).

Helper Plasmids.

The plasmid pDGM6 encodes Rep, Cap and adenovirus helper functions (Gregorevic, P., et al., *Nat. Med.* 10:828-834 (2004)). pLadeno5 contains adenovirus E2A, E4, and VA RNA regions to provide helper functions. pMTrep2, pMTrep6, and pCMVcap6 (Halbert, C. L., et al., *J. Virol.* 75:6615-6624 (2001)) were also used to supply packaging functions. All AAV vectors were made using the cap gene from AAV serotype 6.

The plasmid pDGM6Acap was made by removing the SwaI/BstZ171 cap fragment of pDGM6. The AAV vector plasmids were propagated in the bacterial strains Sure (Stratagene) or JC8111 (Boissy, R., and Astell, C. R., *Gene* 35:179-185 (1985)), and the packaging and helper plasmids were propagated in the DH5a strain of *E. coli*.

AAV Vector Production and Characterization.

AAV-6 vectors were generated by cotransfection of vector and helper plasmids, as shown in Table 1, into 293 cells seeded at $4 \times 10^6$ cells per 10-cm dish the prior day. For the 2-plasmid protocol, the plasmid pDGM6 was co-transfected with the vector plasmids for generating the AAV vectors (20 µg and 10 µg per plate of 293 cells, respectively). For the 4-plasmid protocol, plasmids pLadeno5, pCMVcap6, pMTrep2 (or pMTrep6), described in Halbert C. L. et al., J. Virol 75:6615-6625 (2001), hereby incorporated herein by reference, were used to supply helper and packaging functions (5 µg of each plasmid per plate of cells). Concentration and purification of AAV vectors was done as described in Halbert, C. L., and Miller, A. D., *Methods Mol. Biol.* 246:201-212 (2004)), hereby incorporated herein by reference, except that the centrifugation step in sucrose prior to loading on to a heparin column was omitted.

Southern blot analysis was carried out as described in Halbert, C. L., et al., *J. Virol.* 71:5932-594 (1997) to determine the number of vector genomes (vg) in the AAV vector preparations. It was determined that the AAV-6 vector preparations described in Examples 1-4 herein had generally between $10^{11}$ and $10^{12}$ vg per ml with a vg to FFU ratio in HTX target cells of $2 \times 10^4$ to $5 \times 10^4$ for the AP-expressing vectors, and $10^5$ for the βgal-expressing vector.

Quantitative PCR.

Virus was prepared for qPCR by treating $10^{10}$ to $10^{11}$ genome-containing virions (determined by Southern analysis) with benzonase (100 units per reaction, 5 mM Tris pH 8.0, 10 µg/ml bovine serum albumin, 0.1 mM $MgCl_2$) in 500 µl volume for 1 h at 37° C. Next, AAV virion DNA was extracted by treatment with proteinase K (100 ng/ml) and 50 µl 1 of 10×SET buffer (10% SDS, 1 M Tris pH 7.5, 0.05 M EDTA pH 8.0) for 1 h at 50° C., followed by two phenol/chloroform extractions, and precipitated with 5 µg tRNA and 0.1 M NaCl in ethanol. Virion DNA pellets were resuspended in 100 µl distilled water.

A qPCR assay was carried out as follows: Maxima SYBR Green/ROX kit (Fermentas, Burlington, Canada) was used for the detection of rep and cap genes using the ABI 7900HT Real Time PCR System. Each reaction was done in triplicates with 25 µl volumes containing 12.5 µl of 2× master mix, 150 nM of each primer, and 1 µl template (resuspended vector DNA). The primers RepF (CGGGGTTTTACGA-GATTGTG (SEQ ID NO:10), nucleotide positions 326-345) and RepR1 (CGCCATTTCTGGTCTTTGTG (SEQ ID NO:11), nucleotides 742-721) were used for amplification of rep yielding a 416 bp PCR product and primers CapF (CCACAAGAGCCAGACTCCTC (SEQ ID NO:12), nucleotides 2655-2674) and CapR540 (GCCATCAT-TCGTCGTGACC (SEQ ID NO:13), nucleotides 3193-3175) were used for cap gene amplification giving a 539 bp product. Cycling conditions were 95° C. for 10 min, followed by 40 cycles of 95° C. for 30 s, 55° C. for 1 min, and 72° C. for 40 s. Plasmid pDGM6 representing $10^2$ to $10^6$ copies was used to generate the standard curve to calculate the copy number in the samples for both rep and cap (linearized with NotI for 1 of 2 cap reactions and both rep reactions).

Primers for canine FIX and for βgal were used to determine the amount of vector genomes in reaction. For cFIX, primers cFIXF1 (CCACTGTATTGAGCCTGATGTTAAA) (SEQ ID NO:14) and cFIXR2 (GCTCTGTATGTTC-CCTCTTCTCGGT) (SEQ ID NO:15) were used, and pCM-VcFIX was used for standardization. For βgal, primers lacZqF1 (GCGTTAACTCGGCGTTTCAT) (SEQ ID NO:16) and lacZqR1 (GCGCTCAGGTCAAATTCAGAC) (SEQ ID NO:17) were used, and pACZn was used for standardization. All other AAV vectors used values previously determined by Southern analysis. When comparisons were available, vector genome values derived by Southern analysis and by qPCR varied by less than 2-fold.

Comparison of the Rate of AAV-Mediated Transduction of a Gene that Encodes Human Placental Alkaline Phosphatase (AP), Either Flanked by ITRs in the Standard AAV Vector Configuration (Designated pARAP4), or without any Flanking AAV Sequences (pRAP).

In this experiment, we compared the rate of AAV-mediated transduction of a gene that encodes human placental alkaline phosphatase (AP), either flanked by AAV ITRs in the standard AAV vector configuration (pARAP4), or without any flanking AAV sequences (pRAP). AAV virions were produced by cotransfection of each of these plasmids with a plasmid that expresses AAV Rep and Cap and adenovirus helper proteins (pDGM6) and the virions were purified by using heparin columns. HTX cells were then exposed to the purified AAV preparations and foci of AP-positive cells were quantitated.

Results:

Table 2 shows the results of AAV vector transduction in HTX cells of AAV vector virions containing an AP gene with or without flanking AAV terminal repeats (ITRs), measured in AP+ FFU produced in HTX cells exposed to the purified AAV preparations. The results shown in Table 2 are the means of duplicate determinations in a representative experiment.

TABLE 2

Gene transfer in HTX cells after exposure to AAV vector preparations made using the AP gene with and without flanking AAV terminal repeats[a]

| Transfected plasmids used to generate AAV vector preparations | AP+ foci produced in HTX cells per transfected 10-cm dish: | |
|---|---|---|
| | before benzonase treatment | after benzonase treatment |
| pARAP4 + pDGM6 | $1.5 \times 10^7$ | $1.3 \times 10^7$ |
| pRAP + pDGM6 | $7.5 \times 10^2$ | $3.6 \times 10^2$ |
| pRAP + pUC18 | 0.25 | 0.25 |
| pRAP + pUC18, pDGM6 + pUC18[b] | Not done | 0.30 |
| pRAP + pACZn + pDGM6 | Not done | $1.8 \times 10^3$ |

[a]293 cells were transfected with the indicated plasmids one day after seeding the cells in 10-cm dishes. Three days after transfection, AAV virions were harvested and purified as described above. Purified virions were left untreated or were treated with benzonase to remove DNA that might be bound to the outside of virions. Virions capable of expressing AP were measured using HTX cells as targets for infection. Results are means of duplicate determinations in a representative experiment.
[b]293 cells in 10-cm dishes were independently transfected with pUC18 and pRAP, or pUC18 and pDGM6. After harvest of cells and medium, cell lysates were combined, treated with benzonase, co-purified on a heparin column, and then assayed for AP+ FFU.

As shown in Table 2, AAV vector made with the plasmid that does not contain AAV sequences (pRAP) did indeed induce AP+ foci in HTX cells (Table 2, row 2). However, the number of AP+ foci produced by AAV virus made with the pRAP plasmid was 4 to 5 orders of magnitude lower than that of the standard vector plasmid pARAP4 (Table 2, row 1), which contains the AP gene flanked by AAV ITRs. AAV vector preparations made with a control plasmid (pUC18) instead of the plasmid encoding AAV Rep and Cap proteins (pDGM6) exhibited low levels of background AP+ foci (see Table 2, row 3), as expected.

To test the possibility that the pRAP DNA was transferred to HTX cells by binding to the surface of the AAV virions, AAV vector preparations were treated with benzonase to destroy DNA outside of the virions and were repurified on heparin columns. As further shown in Table 2, benzonase treatment did not destroy the ability of virions made with pRAP to transduce target cells, indicating that the AP gene without the ITR sequences was packaged within the AAV virions (see Table 2, columns 2 and 3).

To further rule out transfer of pRAP DNA to HTX cells via an interaction with the surface of the capsid, two separate cell lysates were made, one from 293 cells transfected with only the non-ITR pRAP plasmid and one from cells transfected with only the helper plasmid expressing the AAV capsid proteins. The two preparations were combined, treated with benzonase and purified. As shown in Table 2, infection of HTX cells with the combined preparation yielded only low background levels of AP, showing that the transfer of AP that we observed in the HTX cells could not be explained by interactions between DNA and fully formed particles (see Table 2, row 4).

We next tested whether transfer of the AP gene from AAV vector generated using pRAP (non-ITRs) would still occur in competition with a genuine AAV vector (containing ITRs), to address the possibility of transfer of genes without AAV ITR sequences during routine AAV vector production. For this experiment, we used the AAV vector ACZn that expresses a nuclear-localized β-galactosidase (βgal) flanked by ITRs to allow independent quantitation of gene transfer by pRAP and the AAV vector ACZn. As shown in Table 2, indeed, the AP gene was transferred by virus produced by cotransfection of pRAP, pACZn and pDGM6 (see Table 12, row 5). The rate of AP gene transfer was 5-fold higher in the presence of the ACZn AAV vector than in its absence, while the titer of the ACZn vector produced in the presence of pRAP was similar to that of other preparations made without it ($2.5 \times 10^5$ βgal$^+$ focus-forming units (FFU) per 10-cm dish), data not shown. These results demonstrate that genes without flanking AAV ITRs are packaged in AAV vector virions and transferred and expressed in cells infected by AAV vector virions.

Conclusion:

In summary, the above experiments confirm that DNA sequences without flanking AAV ITRs can be packaged into AAV virions, and in this case, are transferred and expressed at a rate that is 4 to 5 orders of magnitude lower than that of a typical AAV vector that contains DNA that is flanked by ITRs.

Example 2

This Example demonstrates that DNA encoding Rep and Cap originating from helper plasmids that do not contain flanking ITR sequences are packaged into AAV vector virions and expressed in cells infected with such virions.

Rationale:

The results described in Example 1 suggest that genes without flanking AAV ITRs, such as plasmids used for expression of Cap and Rep during AAV vector production, could be packaged into AAV vector virions and expressed in cells infected with such virions. To further address this issue, we first tested for the presence of cap and rep DNA in several AAV vector preparations by qPCR. We then developed a Cap and Rep complementation assay to determine whether the packaged cap and rep DNAs were expressed in infected cells, as described below.

1. qPCR Analysis for the Presence of Cap and Rep DNA in Several AAV Vector Preparations Methods:

AAV vector preparations were made using the AAV vectors and helper plasmids as indicated in Table 3, using the methods described in Example 1. The AAV preparations were generated using either the single plasmid pDGM6 or using a combination of the plasmids pMTrep2, pCMVcap6, and pLadeno5, as described in Example 1. The plasmid pDGM6 carries rep, cap and adenovirus helper genes, while pLadeno5 carries only the adenovirus help genes. The genes carried by the AAV vectors are as follows: ACWRZn, LacZ; ARAP4, alkaline phosphatase; ACAGhAAT, human alpha1-antitrypsin; ACF3'B, the 3' half of the CFTR coding region.

Virus was prepared for qPCR by treating $10^{10}$ to $10^{11}$ genome-containing particles (determined by Southern analysis) with benzonase as described in Example 1. Next, virion DNA was extracted and was subjected to qPCR as described in Example 1.

Results:

Table 3 shows the quantitation of rep and cap DNA present in AAV vector virions as measured by qPCR analysis. The results shown in Table 3 are expressed as copies of DNA per $10^6$ vector genomes (vg) as determined by Southern blot analysis. For the ACWRZn vector, the genome number was checked by qPCR after benzonase treatment and purification of virions, and was 63% of the value determined by Southern analysis. Results are means of two experiments done in triplicate. The primers used to detect cap and rep DNA, are described in Example 1, and amplify products of 539 and 416 base pairs, respectively.

TABLE 3

Quantitation of rep and cap DNA in AAV vector virions by qPCR$^a$

| AAV vector | Adenovirus helper plasmid | rep and cap plasmids | Copies of cap per $10^6$ vg | Copies of rep per $10^6$ vg |
| --- | --- | --- | --- | --- |
| ACWRZn | pLadeno5 | pMTrep2, pCMVcap6 | 170 | 150 |
| ARAP4 prep 1 | pLadeno5 | pMTrep2, pCMVcap6 | 58 | 70 |
| ARAP4 prep 2 | pLadeno5 | pMTrep2, pCMVcap6 | 14 | 16 |
| ARAP4 prep 3 | pLadeno5 | pMTrep2, pCMVcap6 | 36 | 32 |
| ARAP4 prep 4 | pDGM6 | pDGM6 | 32 | 38 |
| ACAGhAAT prep 1 | pDGM6 | pDGM6 | 26 | 27 |
| ACAGhAAT prep 2 | pDGM6 | pDGM6 | 49 | 63 |
| ACF3'B | pDGM6 | pDGM6 | 7.0 | 9.1 |

$^a$Vector preparations were made by transfections of HEK 293 cells with the indicated vectors and separate plasmids encoding Rep, Cap, and adenovirus helper functions, or with the indicated vectors and a single plasmid, pDGM6, encoding Rep, Cap and adenovirus helper functions. Virus was prepared for qPCR by treating $10^{10}$ to $10^{11}$ genome-containing particles (determined by Southern analysis) with benzonase. Next, virion DNA was extracted as described in Example 1 and was subjected to qPCR that amplifies a 539 base pair region of the cap gene or a 416 base pair region of the rep gene. Results are expressed as copies of DNA per $10^6$ vector genomes as determined by Southern analysis.

As shown in Table 3, the qPCR results showed that vector virions contained 7 to 170 copies of cap DNA and 9 to 150 copies of rep DNA were packaged for every million vector genomes (i.e., at levels of 0.0007% to 0.017% of the level of vector DNA). The rate of both cap and rep DNA packaging was similar for each vector preparation tested, and correlated inversely with the AAV vector yield; i.e., AAV vectors that routinely had higher production yields (e.g., ACF3'B) showed less rep and cap DNA packaging, while those AAV vectors with lower yields (e.g., ACWRZN) had more rep and cap DNA packaging.

These results are consistent with a model in which the rate of cap and rep DNA packaging is constant and independent of AAV vector packaging, and that normalization of cap and rep copy number to the vector copy number generates this inverse relationship. It is noted that the AAV vector preparations tested were made using the single plasmid pDGM6 or using plasmids pMTrep2, pCMVcap6, and pLadeno5, and we found cap and rep DNA in virions made with either plasmid combination. One vector (ARAP4) was made with both methods, and we did not observe a difference in packaging of cap or rep DNA due to the helper plasmids used.

2. Development of a Sensitive Cap and Rep Complementation Assay to Determine if Packaged Cap DNA is Expressed in Cells Infected with AAV Vectors Methods:

Complementation Assay:

To determine whether the packaged cap and rep DNAs are expressed in vector infected cells, we developed a Cap and Rep complementation assay, as illustrated in FIG. 1. In this assay, purified, benzonase treated AAV vector preparations (ACF3'B and ACAGhAAT) were made as described in Example 1. 293 cells were plated at $5 \times 10^6$ cells per 10-cm dish (day 0). The 293 cells were then infected on Day 1 with the purified benzonase-treated AAV vector preparations for 2 h and then the media was replaced to remove benzonase and residual vector. Soon afterwards, the cells were transfected with the plasmid combinations shown below in Table 4 that included various combinations of an AP-expressing AAV vector plasmid (pARAP4) and the plasmids used for AAV vector production. As a positive control, the AAV vector and all three AAV production plasmids were used, while remaining combinations lacked one or more plasmids. On day 2, the transfection/infection medium was aspirated and replaced with medium with 2 mM added L-glutamine. On day 4, cells and medium were harvested, freeze/thawed 3 times, centrifuged to remove cell debris, and was frozen in 1 ml aliquots. Prior to infection of HTX cells, 1 ml of cell lysate was thawed and treated for 2 h with benzonase. Then the transducing titer of each cell lysate was determined by quantitating AP$^+$ FFU on HTX cells. HTX cells were plated at $5 \times 10^4$ cells per well in 6-well dishes on day 0. The following day, medium was aspirated, cells rinsed once with PBS containing calcium and magnesium, then exposed to 500 µl of cell lysate with 500 µl of DMEM for 2 h, then 1 ml of DMEM containing 20% FBS was added. The cells were fixed and stained for AP expression 3 days later. Production of AP$^+$ HTX cells using plasmid combinations lacking cap and/or rep DNA would indicate provision of these functions by the AAV vector stock used initially to infect the 293 cells.

Results:

Several AAV vectors, including ACF3'B and ACAGhAAT, were examined using the complementation assay and the results are shown in Table 4. The results shown in Table 4 are means of duplicate determinations.

As further shown in Table 4, the complementation assay also detected transfer of cap gene function by the second vector preparation, ACAGhAAT. In two experiments, using $7 \times 10^{10}$ vg ACAGhAAT for each infection, an average vector titer of $5.8 \times 10^3$ AP$^+$ FFU per ml was observed after transfection of plasmid combination #2 (that lacks the Cap expression plasmid). No production of AP vector was seen from transfection combination #3 that lacked rep, showing that rep function was not transferred by the ACAGhAAT vector.

Note that when no AAV vector preparation was added in the above experiments, the plasmid combination that did not contain the cap construct produced 36, 66 and 89 AP$^+$ FFU per ml (Table 4, experiments 1-3, plasmid combination #2). This was higher than the background AP values observed in combinations 3, 4 and 5, and we hypothesize that this is due to AP protein transfer (pseudotransduction). The Rep protein in this combination likely caused replication of the ARAP4 vector DNA resulting in higher levels of AP protein in the lysate added to the target cells.

To test whether cap function could be transferred by an AAV vector with a different AAV serotype, we tested for transfer of cap function by an AAV vector packaged with AAV6 or AAV2 capsid proteins, and found vectors with both serotypes transferred cap gene function (Table 4, Exp. 4). In one case we also detected transfer of rep gene function, indicating that both the cap and rep genes can be transferred and expressed, as might have been expected based on the presence of both cap and rep gene sequences in AAV virions

TABLE 4

Results of Complementation Assay: Transfer of Cap and Rep function following infection with AAV vectors[a]

| | | | AP FFU per ml for plasmid combination: | | | | |
|---|---|---|---|---|---|---|---|
| | | | 1 | 2 | 3 | 4 | 5 |
| | | | pLadeno5 | + | + | + | + |
| | | | pMTrep6 | + | − | − | − |
| | | Amount | pCMVcap6 | − | + | − | − |
| Expt | AAV vector | (vg) | pARAP4 | + | + | + | − |
| 1 | ACF3'B (AAV6) | $2 \times 10^{12}$ | ND | $1.0 \times 10^4$ | ND | 1 | 3 |
| 1 | | none | ND | 36 | ND | ND | ND |
| 2 | ACAGhAAT (AAV6) | $7 \times 10^{10}$ | ND | $4.5 \times 10^3$ | ND | 4 | 6 |
| 2 | | none | $1.2 \times 10^6$ | 66 | 17 | ND | ND |
| 3 | ACAGhAAT (AAV6) | $7 \times 10^{10}$ | ND | $7.1 \times 10^3$ | 8 | 4 | 6 |
| 3 | | none | ND | 89 | ND | ND | ND |
| 4 | ACWRZn (AAV6) | $7 \times 10^{10}$ | $3.6 \times 10^5$ | $3.1 \times 10^4$ | $3.9 \times 10^3$ | ND | ND |
| 4 | ACWRZn (AAV2) | $7 \times 10^{10}$ | $4.4 \times 10^5$ | $1.4 \times 10^4$ | 8 | 5 | ND |
| 4 | | none | $5.5 \times 10^5$ | <1 | 2 | ND | ND |

[a]Cap and Rep complementation assays were done as shown in FIG. 1 and described above, except that the crude cell lysate was filtered (0.2 µm-pore-size) to reduce background AP in experiment 4. Results are means of duplicate determinations.

Transfection by the complete set of plasmids resulted in the production of ARAP4 vector virus (plasmid combination #1). Importantly, infection with the ACF3'B AAV vector preparation followed by transfection with plasmid combination #2 (that contained vector, replication and helper functions but lacked a capsid-expressing plasmid), yielded $10^4$ AP$^+$ FFU per ml of lysate, indicating transfer of functional cap genes by the ACF3'B vector. Only background levels of AP$^+$ foci were observed with plasmid combinations #4 or #5.

(Table 3). We note that in this experiment, we filtered the virus produced by the transfected 293 cells in an attempt to reduce transfer of AP protein (pseudotransduction). Indeed, this substantially reduced the background AP+ foci obtained for plasmid combination 2 when no AAV vector was used.

Conclusion:

The results described in this Example demonstrate that AAV vector preparations contain cap DNA, which can be expressed in infected cells, and may serve as an immunogen in animals.

Example 3

This Example demonstrates that the insertion of a large intron into the cap gene of a packaging plasmid to generate a capsid expression cassette (cap+intron="captron") that is too large for packaging into AAV virions is effective to eliminate transfer of capsid-expressing DNA in AAV vector transduced cells.

Rationale:

One feature of AAV vectors, often considered to be a limitation, is their small packaging capacity (limited to packaging DNA in the size range below about 4.7 to 5 kb). The inventors have exploited this size limitation in a strategy to minimize the packaging of functional cap genes in which expression of capsid in transduced cells is limited by introducing an intron into the capsid expression cassette (e.g., between the cap gene and the promoter) such that the expression cassette would be too large to package into AAV virions. This Example describes the generation of a captron construct in which a large intron (4.3 kb) from the 5' untranslated region of the human EIF2S1 gene was inserted between the CMV promoter and the alternatively spliced intron in the AAV cap gene.

Methods:

1. Generation of Intron-Containing Cap Expression Constructs.

A large intron (4.3 kb) from the 5' untranslated region of the human EIF2S1 gene was inserted between the CMV promoter and the alternatively spliced intron in the AAV cap gene to make the plasmid pCMVEcap6 (FIG. 2a). The 4,460 bp region including the 5' untranslated region intron from the human EIF2S1 gene was cloned by PCR amplification of DNA from the HTX cell line using primers EIF2S1inFN (GGCTAGCgcggtggagtgagcgaag) (SEQ ID NO:18) and EIF2S1inRN (GGCTAGCttctgcaatttaaacaaaag) (SEQ ID NO:19) and inserted into the NheI site in pCMVcap6 to generate pCMVEcap6. Unfortunately, this plasmid did not express functional capsid protein, as determined by a Western blot analysis (FIG. 2b), and further investigation using northern analysis and RT-PCR revealed that the EIF2S1 intron prevented proper excision of the native AAV intron (data not shown).

A new construct with a hybrid EIF2S1/AAV intron was generated by removing a 200 bp fragment containing the EIF2S1 splice acceptor and the AAV splice donor to make the plasmid pCMVE2cap6 (SEQ ID NO:7), illustrated in FIG. 2C. The pCMVE2cap6 construct was generated by removal of a 200 bp KpnI fragment of pCMVEcap6 containing the splice acceptor from the EIF2S1 intron and the splice donor of the AAV cap gene. The size of this gene from promoter to the end of the cap ORF is about 7.5 kb, much larger than the 4.7 kb AAV packaging limit. Western blot analysis shown in FIG. 2B, was carried out on cell lysates of 293T cells transfected with 10 µg DNA using anti-AAV VP1+VP2+VP3 mouse monoclonal antibody (American Research Products). 10 ul of lysate was loaded per lane.

Figure 2B:
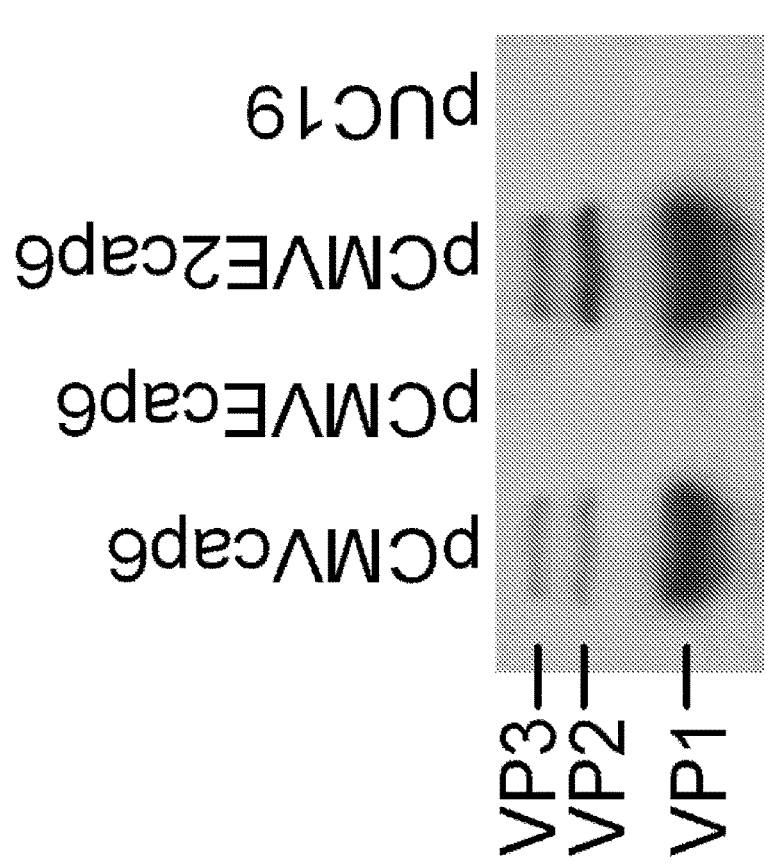
FIG. 2B is a Western blot of cell lysates of 293T cells transfected with 10 ng DNA using an anti-AAV VP1+VP2+VP3 mouse monoclonal antibody, with 10 µl lysate loaded per lane; showing cap expression resulting from the cap6 expression cassettes illustrated in FIG. 2A, as described in Example 3.
Figure 2C:
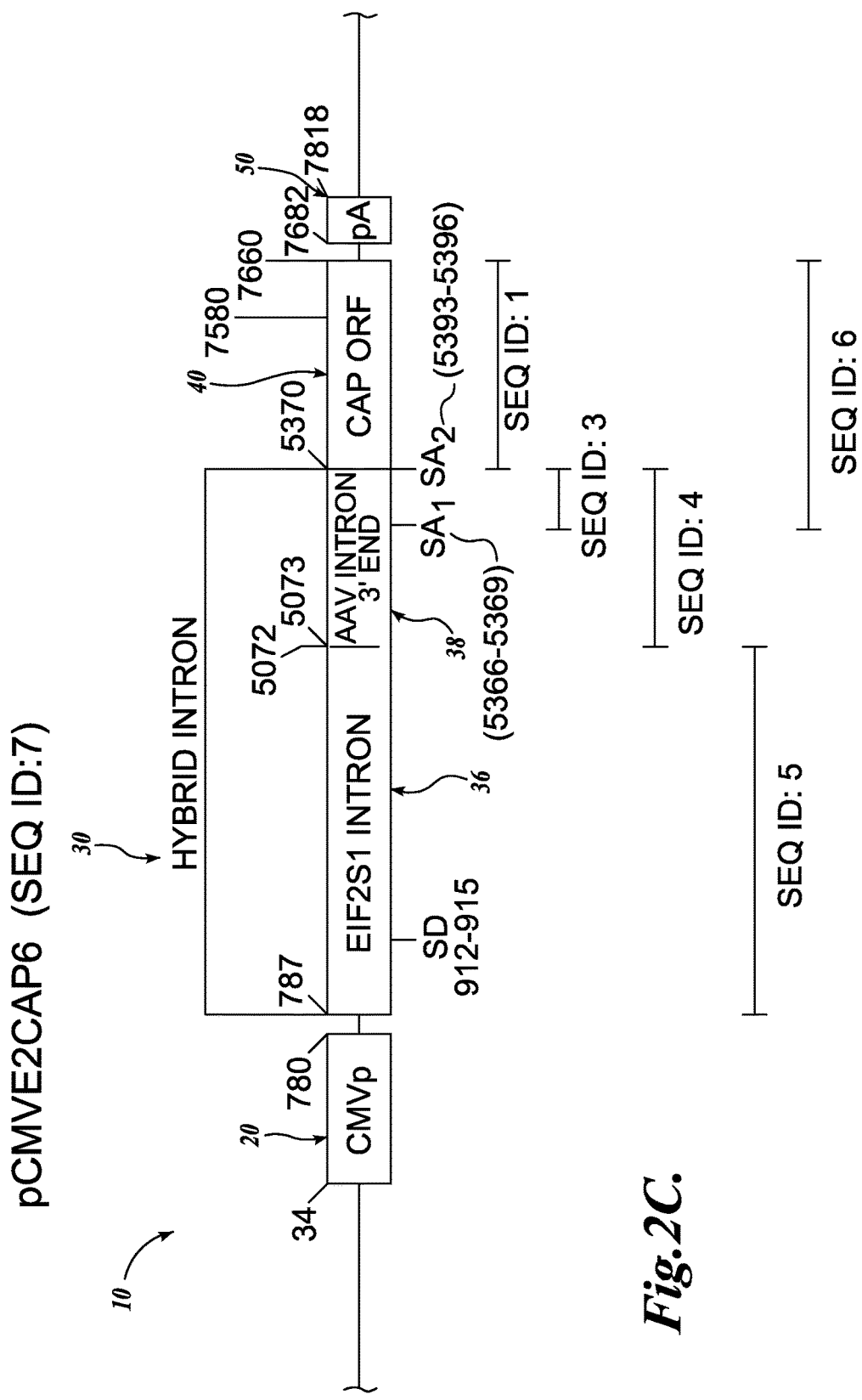
FIG. 2C illustrates the elements of a representative expression cassette comprising a nucleotide sequence encoding the cap6 ORF, designated "pCMVE2cap6," as described in Example 3.

As shown in FIG. 2b, the pCMVE2cap6 construct expressed all three capsid forms, verifying proper alternative splicing at the AAV splice acceptors.

2. Titer of AAV Preparations Made Using the Intron-Containing Cap Constructs (Captron)

The titer of AAV preparations made using the intron-containing cap constructs were compared as follows. Crude AAV lysates were collected three days after transfection of 293T cells with 4 µg pARAP4, 4 µg pDGM6Δcap and 2 µg of a cap plasmid (pCMVcap6, pCMVEcap6 or pCMVE2cap6). Cells and medium were freeze/thawed three times, centrifuged at 1,000×g for 10 minutes to remove cells and debris, and filtered (0.2 µM-pore-size). ARAP4 titers from one experiment were determined by infecting HTX cells and staining for AP+ foci after three days. As shown in Table 4, only a minor change was observed in yield between pCMVE2cap6 and pCMVcap6, even though the 2 µg of pCMVE2cap6 transfected contains about half as many copies as that of the 2 µg of pCMVcap6.

TABLE 5

| ARAP4 vector titer | |
|---|---|
| cap plasmid used | AP+ FFU/ml |
| pCMVcap6 | $3.0 \times 10^6$ |
| pCMVEcap6 | $1.5 \times 10^4$ |
| pCMVE2cap6 | $2.0 \times 10^6$ |
| pUC19 control | 40 |

3. Measuring Rep and/or Cap Gene Contamination by the Complementation Assay

The Cap and/or Rep complementation assay, as described in Example 2, was used to test the effect of the intron on capsid expression by comparing parallel AAV productions made with pCMVcap6 and the captron plasmid, pCMVE2cap6. The results are shown in Table 6.

TABLE 6

Inclusion of a large intron in the cap gene (AAV captron vector) prevents transfer of Cap function in transduced cells, as determined by the complementation assay[a]

| | | | ARAP4 vector production (AP+ FFU per ml) after transfection with plasmid(s) combination: | | | |
|---|---|---|---|---|---|---|
| | | | 1 | 2 | 3 | 4 |
| AAV vector used for preinfection | cap plasmid used for vector production | Vector Amount (vg) | pARAP4 pCMVcap6 pMTrep6 pLadeno5 | pARAP4 – pMTrep6 pLadeno5 | pARAP4 pCMVcap6 – pLadeno5 | pARAP4 – – pLadeno5 |
| ACZn | CMVcap6 | $7 \times 10^{10}$ | $9 \times 10^4$ | $5.3 \times 10^2$ | 0 | 0 |
| ACZn | Captron (pCMVE2cap6) | $7 \times 10^{10}$ | $1 \times 10^5$ | 2 | 1 | 1 |
| None | None | None | $6 \times 10^4$ | 0 | 0 | 0 |
| ACMVcFIX | CMVcap6 | $7 \times 10^{10}$ | $1.6 \times 10^5$ | $2.8 \times 10^3$ | 3 | 3 |
| ACMVcFIX | Captron (pCMVE2cap6) | $7 \times 10^{10}$ | $1.9 \times 10^5$ | 3 | 1 | 3 |
| None | None | None | $2.2 \times 10^5$ | 2 | 3 | 1 |

TABLE 6-continued

Inclusion of a large intron in the cap gene (AAV captron vector) prevents transfer of Cap function in transduced cells, as determined by the complementation assay[a]

| AAV vector used for preinfection | cap plasmid used for vector production | Vector Amount (vg) | ARAP4 vector production (AP+ FFU per ml) after transfection with plasmid(s) combination: | | | |
|---|---|---|---|---|---|---|
| | | | 1 pARAP4 pCMVcap6 pMTrep6 pLadeno5 | 2 pARAP4 – pMTrep6 pLadeno5 | 3 pARAP4 pCMVcap6 – pLadeno5 | 4 pARAP4 – – pLadeno5 |
| ACF3'B | CMVcap6 | $3.8 \times 10^{11}$ | ND | 41 | 0 | 0 |
| ACF3'B | Captron (pCMVE2cap6) | $3.8 \times 10^{11}$ | ND | 0 | 3 | 3 |

[a]HEK 293 cells were plated at $5 \times 10^6$ cells per 10-cm dish on day 1. On day 2, cells were preinfected with the indicated amounts of purified AAV vectors made using either the standard cap plasmid (pCMVcap6) or the captron (intron-containing) cap plasmid (pCMVE2cap6), or were left uninfected. All vector preparations were treated with benzonase before use to remove non-encapsidated DNA. The virus and medium was removed from the cells two hours later and cells were re-fed with fresh media. One hour later the cells were transfected with plasmid combinations as indicated. pUC13 insert plasmid DNA was used to replace the DNA of any missing plasmid. On day 3, the medium was aspirated and cells were re-fed. On day 5, cells and medium were harvested (10 ml), freeze/thawed 3 times, centrifuged, and filtered to remove cell debris. Next, the cell lysate was treated with benzonase to remove extraneous DNA. The number of functional ARAP4 virions in the cell lysates were then determined by measuring AP+ focus-forming units (FFU) using HT-1080 human fibrosarcoma cells as targets for transduction. Results are means from one experiment done in duplicate (ACZn and ACF3'B) and means from two, five or four experiments done in duplicate (ACMVcFIX made with the CMVcap6 plasmid, the captron plasmid or none, respectively). Genes carried by AAV vectors; ACZn, LacZ; ACMVcFIX, canine clotting factor IX, ACF3'B, the 3' half of the CFTR coding region.

As shown in Table 6, transfection of cells with all 4 plasmids produced lysates with similar titers regardless of whether a standard vector, a captron vector, or no AAV vector was used to infect the cells (Table 6, combination 1), showing that prior infection of 293 cells with an AAV vector did not inhibit production of AAV virions. No transfer of AP was seen without rep (Table 6, combination 3), or without rep and cap (Table 6, combination 4). Cells infected with ACZn and ACMVcFIX AAV preparations made using the original pCMVcap6 did demonstrate expression of Cap protein by production of ARAP4 AAV vector (Table 6, combination 2). In contrast, cells infected with AAV preparations made using the captron plasmid did not produce Cap protein, as only a very low, background level of AP+ cells was observed (Table 6, combination 2). The third vector, ACF3'B, routinely had at least a 10-fold higher vector yield than other vectors, and therefore a lower cap to vg ratio. When $7 \times 10^{10}$ vg was used for infection, no complementation was observed (data not shown). When 5-fold more vector was used, ACF3'B made with pCMVcap6 showed a detectible level of cap complementation while the AAV preparation made with the captron construct still exhibited no detectible transfer of cap function (Table 6). In summary, inclusion of a large intron sequence in the cap construct reduced Cap expression from all AAV vectors tested to undetectable levels as measured by this highly sensitive complementation assay.

4. qPCR Analysis of Rep and Cap DNA Present in AAV Vector Preparations

Presumably, fragments of the DNA encoding the cap gene are still packaged into AAV vector virions, but not in large enough sizes to allow cap gene transfer and expression. This hypothesis was confirmed by measuring cap and rep DNA via qPCR analysis in several vector preparations made with either the standard pCMVcap6 plasmid or the captron plasmid. Analysis of DNA from AAV vector virions by qPCR showed that both cap and rep DNA sequences were still packaged (Table 7). However, there was a trend toward reduced packaging of cap in vector preparations with the captron construct. The amount of packaged rep DNA was not affected by use of the captron plasmid. For each of the three captron vectors investigated, copies of cap were 1.5-2 fold lower than rep copies, whereas no significant difference in cap and rep packaging was observed in vectors made with pCMVcap6.

TABLE 7

Quantitation of rep and cap DNA sequences in AAV virion preparations made with the standard cap or the captron cap plasmids

| AAV vector | cap plasmid used during production | Copies of cap per $10^6$ vg | Copies of rep per $10^6$ vg |
|---|---|---|---|
| ACZn | CMVcap6 | 240 | 240 |
| ACZn | Captron | 54 | 110 |
| ACF3'B | CMVcap6 | 4.1 | 9.5 |
| ACF3'B | Captron | 9.8 | 15 |
| ACMVcFIX | CMVcap6 | 140 | 150 |
| ACMVcFIX | Captron | 55 | 110 |

[a]Virion DNA was prepared for qPCR as described for Table 3 and in Example 2. Vector genomes were quantitated by Southern analysis for the ACF3'B vector and by qPCR for the ACZn and ACMVcFIX vectors by using primers for βgal or cFIX, respectively. Results are means of two experiments done in triplicate. Results for ACMVcFIX are means of experiments using two different vector preparations.

5. qPCR Analysis to Detect Cap mRNA in AAV Vector-Exposed Cells

We next used a qRT-PCR assay to detect cap mRNA in virus-exposed cells and to confirm the cap complementation assay results by using a second method.

Methods:

HTX cells were infected with an AAV6 vector (ACMVcFIX) made with either pCMVcap6 plasmid or the captron plasmid pCMVE2cap6 at an MOI of $4 \times 10^6$ vg per cell. To maximize sensitivity, HTX cells were infected at a multiplicity of infection (MOI) of $4 \times 10^6$ vg of ACMVcFIX vector per cell and 300 ng of total RNA from virus-exposed cells was used per qRT-PCR reaction. Total RNA was extracted using TRIZOL (Invitrogen) after three days. The RNA was treated with DNase and cDNA was synthesized using an oligo $(dT_{20})$ primer using SuperScript III Reverse Transcriptase (Invitrogen). qRT-PCR was conducted in triplicate using Maxima SYBR Green qPCR master mix (Fermentas) with cDNA from 300 ng of RNA. The primers and standards for cap and cFIX were the same as those used for the above qPCR analysis of virion DNA, except that both pDGM6 and pCMVcFIX standards were linearized for all reactions (with NotI and HindIII, respectively). All standard curve reactions included cDNA made from uninfected HTX cells in addition to the known amounts of linearized plasmid. All primers were used at 0.2 µM and cycle conditions for both reactions were 95° C. for 10 min, with 45 cycles of 95° C. for 15 s and 60° C. for 1 min, followed by a dissociation curve.

Results:

No cap mRNA could be detected from cells infected with the vector made with the captron construct in any of the triplicate reactions. However, in qRT-PCR reactions done on two mRNA samples from independent infections with AAV made using pCMVcap6, approximately one copy per reaction was detected in one of the triplicate reactions (2/6 positive reactions, with the correct size amplicon confirmed on an agarose gel). Even after 45 cycles, no amplification products were observed in negative controls (300 ng of mRNA from uninfected HTX cells), or in controls performed without RT (to confirm the absence of DNA contamination). These data show that cap mRNA transcribed from cap gene impurities in AAV vectors can be detected by qRT-PCR, and indicate that use of the captron plasmid for vector production eliminated expression of cap mRNA. The level of cFIX mRNA detected in these samples was $4.9 \times 10^5$ copies per reaction, suggesting that cap mRNA is made at a level $10^6$-fold lower than that of the vector transgene. This was at the limit of detection of qRT-PCR, and therefore the result cannot be accurately quantified. However, the result was reproducible and agrees with results from the complementation assay. Thus, data from both the complementation assay and qRT-PCR assays confirm that use of this intron-containing construct eliminated capsid expression from AAV vectors.

Discussion of Examples 1-3

The results described in Examples 1-3 confirm previous reports of contamination of AAV vector preparations with DNA from plasmids lacking AAV sequences, as well as DNA from cap and rep plasmids used to make AAV vectors. However, in contrast to previous results (Hauck, B., et al., Mol. Ther. 17:144-152 (2009)), we show that cap DNA present in AAV vector preparations can express cap mRNA and protein in vector-transduced cells. To detect Cap protein expression, we used a sensitive complementation assay involving infection of AAV vector preparations followed by transfection of various plasmid combinations, and for RNA detection we exposed cells to more vector MOI ($4 \times 10^6$ vg per cell) and analyzed more cell RNA (300 ng) than previously used ($10^5$ vg per cell and 200 ng RNA) in Hauck (2009).

Even though the amount of packaged cap DNA is orders of magnitude less than the vector DNA present in AAV vector preparations produced using standard cap plasmids (i.e., non-intron containing cap constructs)), there may be significant levels of expressed capsid in vivo resulting from infection with standard AAV vector preparations due to the high number of AAV vectors required for therapeutic effect. For example, in the FIX clinical trial in which a capsid-specific response was observed, a dose of up to $2 \times 10^{12}$ vg/kg was used (Manno, C. S., et al., Nat. Med. 12:342-347 (2006)). Thus, our results described in Examples 1-3 herein demonstrate that capsid protein made from cap DNA in AAV preparations are likely to be at least partially responsible for the capsid-directed immune response observed in canine and human clinical trials.

Based on data from canine studies showing a capsid-directed immune response following transient immunosuppression, a significant amount of capsid particles would need to persist for greater than 16 weeks in vivo for the response to be entirely due to administered capsid protein. Indeed, intact AAV virions have been detected up to 6 years after AAV gene transfer in the retina of dogs and primates (Stieger, K., et al., Mol. Ther. 17:516-523 (2009)). The authors in Stieger et al. (2009) hypothesized that the virions were from the initial inoculum, but our data suggest that virions also can be made from newly synthesized capsid proteins, which we have shown can be made in the absence of adenovirus helper functions (Allen J. M. et al., Mol Ther 1:88-95 (2000)).

While investigating strategies to prevent packaging of cap DNA, we noted that traditional methods of AAV vector preparation used capsid expression cassettes small enough to fit within the AAV virion. Many copies of the cap gene are present within the cell following transfection, increasing the possibility for packaging. Alternative methods using cell lines with integrated copies of rep and cap would most likely not circumvent this problem, as it has been shown that efficient expression of AAV from cell lines required amplification of the rep and cap genes out of their integrated form. Contamination of AAV produced from a stable cell line containing ampicillin resistance gene DNA has already demonstrated that packaging of amplified DNA occurs (Chadeuf, G., et al., Mol. Ther. 12:744-753 (2005); Chadeuf, G., et al., J. Gene Med. 2:260-268 (2000); and Liu, X., et al., Mol. Ther. 2:394-403 (2000)). Much work with AAV has also focused on purification methods, such as CsCl centrifugation protocols (Ayuso, E., et al., Gene Ther. 17:503-510 (2010)). These processes can remove DNA that is not packaged in virions and can separate empty particles from DNA-containing particles, which does reduce the amount of injected capsid protein, but it is important to note that particles containing cap DNA are not empty, and are not likely to be completely excluded by any such process.

It has been reported that AAV vectors are able to express large genes by recombination of multiple gene fragments, but this process is relatively inefficient for oversized constructs (Duan, D., et al., Mol. Ther. 4:383-391 (2001); Halbert, C. L., et al., Nat. Biotechnol. 20:697-701 (2002); Dong, B., et al., Mol. Ther. 18:87-92 (2010); Lai, Y., et al., Mol. Ther. 18:75-79 (2010); and Wu, Z., et al., Mol. Ther. 18:80-86 (2010)).

It is also unknown whether the cap DNA fragments recombine at the same rate, or whether vector recombination is due in part to the presence of the AAV ITRs. The requirement of at least two fragments for recombination and the greatly reduced packaging rate of cap gene fragments in comparison to that of AAV vectors argues that recombination events leading to Cap expression should be exceedingly rare. Indeed, we observe no evidence of any capsid expression in cultured cells when using the captron construct. We conclude that AAV made with a large intron-containing cap gene offers a less immunogenic alternative to vectors made with current capsid constructs and may promote longer-term transgene expression in animals and humans compared to previous vectors.

In addition, as would be understood by those of skill in the art, it is expected that the same strategy of introducing one or more introns into a helper plasmid or into a gene expression construct present in an AAV packaging cell, can be utilized to effectively reduce and/or eliminate the packaging of any undesired DNA that is present during AAV virus production into AAV virions, such as DNA encoding the AAV rep gene, a selectable gene such as the gene encoding ampicillin resistance, etc.

Example 4

This Example demonstrates that there is a dramatic reduction in the immune response in dogs after delivery to muscle of a AAV6 vector encoding canine factor IX produced using the captron plasmid in comparison to the immune response observed after infection with an AAV6 vector encoding the same transgene produced using a standard cap plasmid.
Rationale:

Current studies indicate that the main hurdle to using AAV vectors for in vivo gene delivery is the development of host immune responses to AAV proteins and/or the transgene product. These responses can destroy transgene-expressing cells and can limit the efficacy of vector readministration to increase transgene expression. Mice are relatively tolerant of AAV vector-mediated transduction and can express many vector-encoded foreign proteins for long periods. In contrast, robust immune responses to transgene products and to AAV capsid proteins that dramatically limit transgene expression have been demonstrated in dogs (see Halbert, et al., *Mol. Ther.* 18:1165-1172 (2010); Wang, et al., *Hum. Gene Ther.* 18:18-26 (2007); Wang, et al., *Mol. Ther.* 15:1160-1166 (2007), predicting that cellular immunity to AAV vectors will likely be an obstacle in humans. In line with the results observed in murine and canine studies, clinical trials in human subjects have identified problems that are often not observed in small animal models. For example, transient transaminitis developed shortly after vector administration in a trial of hepatic AAV2-mediated factor IX transfer in hemophilia B patients and was accompanied by the rise of AAV2 capsid-specific CD8$^+$ T cells. In this trial, transgene expression was sustained for less than 8 weeks. Manno, C. S. et al., *Nat. Med.* 12:342-347 (2006).

In addition, several immunogenic epitopes of the capsid proteins of AAV2 and AAV8 have been identified in humans (Chen, et al., *Mol. Ther.* 13:260-269 (2006); Manno et al., 2006)). These data indicate that additional studies of immunogenicity of AAV vectors are warranted so that strategies can be developed to permit long-term transgene expression.

The main protein components of AAV vector virions are the capsid proteins. Immune responses against capsid proteins can arise in response to the large amount of AAV vector virions required for effective gene therapy. In addition, although AAV vectors are designed to be replication-defective and are generally assumed to be incapable of production of viral proteins, as demonstrated in Examples 1-3, the standard cap gene expression constructs used to make AAV vectors can be packaged and expressed at low levels in cells exposed to AAV vectors, and could result in long-term stimulation of immune responses against capsid proteins in gene therapy recipients. As further described in Example 3, we have developed a method to prevent cap gene transfer and expression through the use of a Captron construct comprising a Cap expression cassette comprising at least one large intron. In this Example, a study was carried out in a dog model to determine whether this Captron vector alteration results in reduced immune responses concomitant with a reduced need for immunosuppression.

Dogs are the only species commonly used in preclinical studies that has the rare combination of great morphologic diversity and a well-mixed gene pool, as do humans. Further, the canine model has an unexcelled track record of >40 years of translating laboratory work in hematopoietic cell transplantation to the treatment of human patients with malignant and non-malignant blood disorders. The existence of a canine model for DMD, the cxmd dog, provided a model to test directly the efficacy of dystrophin replacement strategies to treat DMD. This Example describes an extended study designed to determine if AAV vectors generated using the captron based packaging system reduces immune responses to AAV vectors designed to treat muscular dystrophy in cxmd dogs as a prelude to human clinical trials.
Methods:

For this study we used an AAV vector encoding canine factor IX (cFIX) driven by a human cytomegalovirus immediate-early promoter. We chose cFIX because this protein can be readily detected in canine muscle, where it is not normally made, and cFIX is not immunogenic in dogs. The cFIX vector was produced in AAV6 capsids by using a standard cap6 expression plasmid (cap6) or one in which a large intron was inserted into the cap6 gene (captron plasmid), as described in Example 3, and were purified on heparin columns, as described in Halbert and Miller, *Methods Mol. Biol.* 246:201-212 (2004), hereby incorporated herein by reference, or by centrifugation in CsCl. AAV6-CMV-cFIX vector titer was determined by quantitating vector genomes (VG). $10^{11}$ or $5 \times 10^{11}$ VG in 250 µl saline was injected per site into the hind-limb biceps muscles of canines underneath non-absorbable sutures to allow accurate biopsy. Canine experiments were performed as described in Wang et al., *Mol. Ther.* 15:1160-1166 (2007), hereby incorporated herein by reference. Biopsies were performed 4 weeks later. Serial sections were examined for analysis of muscle tissue structure and for detection of local mononuclear cell infiltration (i.e., T cell infiltration) using hematoxylin and eosin (H&E) staining and for cFIX expression and the presence of CD8 T-cells by immunohistochemistry.
Results:

Immunohistochemistry and H&E analysis was carried out on muscle biopsy samples obtained four weeks after administration of various preparations of AAV6-CMV-cFIX purified over a heparin column (results summarized in TABLE 8 below), or purified over a CsCl gradient (results summarized in TABLE 9 below).

TABLE 8

Summary of 4 week biopsy histology results for AAV6-CMV-cFIX preparations purified over a heparin Col.

| | $1 \times 10^{11}$ VG generated using standard Cap6 packaging plasmid | $5 \times 10^{11}$ VG generated using Cap6 + intron (Captron) packaging plasmid | $5 \times 10^{11}$ VG generated using Cap6 + intron (Captron) packaging plasmid |
|---|---|---|---|
| cFIX (green stain) | + | + | + |
| H&E (evidence of inflammatory response) | ++ | − | − |
| CD8 (green stain) | ++ | − | − |

TABLE 9

Summary of 4 week biopsy histology results for AAV6-CMV-cFIX preparations purified by centrifugation in CsCl

| | $1 \times 10^{11}$ VG generated using standard Cap6 packaging plasmid | $5 \times 10^{11}$ VG generated using Cap6 + intron (Captron) packaging plasmid |
|---|---|---|
| cFIX (red or green stain) | + | + |
| H&E (evidence of inflammatory response) | ++ | − |
| CD8 (green stain) | ++ | − |

TABLE 8 summarizes the results of immunohistochemistry and H&E analysis of four week biopsy samples after administration to canines of various preparations of AAV6-CMV-cFIX purified over a heparin column. As summarized in TABLE 8 (row 1), approximately equivalent levels of cells (green staining) were found to be expressing cFIX in muscle biopsy samples after transduction with an AAV cFIX vector preparation made using the standard cap6 plasmid as compared to the level of cFIX staining with an AAV cFIX vector preparation made using the captron plasmid. As shown in row 2, a relatively high level of inflammation in muscle biopsy samples was observed after transduction with the AAV cFIX vector preparation made using the standard cap6 plasmid, as determined by H&E staining, in comparison to the nearly complete muscle preservation in biopsy samples and lack of inflammation observed after transduction with the AAV cFIX vector preparation made using the captron plasmid. As shown in row 3, a higher level of CD8 cells (green staining) was observed in the biopsy sample after transduction with an AAV cFIX vector preparation made using the standard cap6 plasmid as compared to the very low level of CD8 cells present after transduction with an AAV cFIX vector preparation made using the captron plasmid.

TABLE 9 summarizes the results of immunohistochemistry and H&E analysis of four week biopsy samples after administration to canines of various preparations of AAV6-CMV-cFIX purified over a CsCl gradient. As summarized in TABLE 9 (row 1), approximately equivalent levels of cells (green staining) were found to be expressing cFIX in muscle biopsy samples after transduction with an AAV cFIX vector preparation made using the standard cap6 plasmid as compared to the level of cFIX staining with an AAV cFIX vector preparation made using the captron plasmid. As shown in row 2, a relatively high level of inflammation in muscle biopsy samples was observed after transduction with the AAV cFIX vector preparation made using the standard cap6 plasmid, as determined by H&E staining, in comparison to the nearly complete muscle preservation in biopsy samples and lack of inflammation observed after transduction with the AAV cFIX vector preparation made using the captron plasmid. As shown in row 3, a higher level of CD8 cells (green staining) was observed in the biopsy sample after transduction with an AAV cFIX vector preparation made using the standard cap6 plasmid as compared to the very low level of CD8 cells present after transduction with an AAV cFIX vector preparation made using the captron plasmid.

These results indicate that a relatively high level immune response occurred in the dogs injected with the AAV cFIX vector prepared using the standard cap6 plasmid and dramatically reduced levels of immune response in the dogs injected with the AAV cFIX vector prepared using the captron plasmid. It is clear that cells transduced with the AAV cFIX vector generated using the captron plasmid express cFIX. It also appears that vector purification by CsCl centrifugation did not reduce the immune response observed in dogs injected with the AAV cFIX vector generated using the standard cap6 plasmid, as compared to the immune response observed with the AAV cFIX vector generated using the standard cap6 plasmid and heparin purification. This is an important result because vector production using heparin columns is more easily scaled up to the quantities required for clinical trials.

Overall Conclusion:

The results described in Examples 1-4 demonstrate that AAV vectors generated using the captron construct, which eliminates capsid gene transfer and capsid expression in transduced cells, are dramatically less immunogenic when administered to a dog at therapeutic in vivo amounts than AAV vectors generated using the standard cap6 construct. In view of these results, it is expected that AAV vectors made using captron plasmids will generate an increase in the number and persistence of cFIX (or other transgenes of interest) positive cells. It is also expected that AAV-captron generated vectors will reduce the level of, or eliminate the need for an immunosuppressive regimen after AAV vector transduction.

While illustrative embodiments have been illustrated and described, it will be appreciated that various changes can be made therein without departing from the scope of the invention.

The invention claimed is:

1. An intron-modified capsid expression cassette useful for generating adeno-associated virus (AAV) vector particles, said expression cassette comprising a polynucleotide comprising:
(a) a nucleic acid molecule encoding an AAV capsid protein operably linked to a promoter and a polyadenylation signal, wherein the encoded AAV capsid protein packages AAV vectors in the presence of rep and adeno helper functions, and
(b) one or more heterologous excisable introns operably linked to the nucleic acid molecule;
wherein said nucleic acid molecule has a length of less than 5 kilobases, and wherein said nucleic acid molecule and said one or more heterologous excisable introns together have a length of more than 5 kilobases, and
wherein the total size of the one or more heterologous excisable introns together is at least 2 kb.

2. The expression cassette of claim 1, wherein the nucleic acid molecule encodes an AAV capsid protein from an AAV serotype selected from the group consisting of AAV-1, AAV-2, AAV-3, AAV-4, AAV-5, AAV-6, AAV-7, AAV-8, AAV-9, AAV-10, AAV-11, AAV-12, and AAV-13, or a variant or hybrid protein thereof.

3. The expression cassette of claim 1, wherein the nucleic acid molecule encodes an AAV capsid protein from an AAV serotype selected from the group consisting of AAV-2, AAV-8, and AAV-6, or a variant or hybrid protein thereof.

4. The expression cassette of claim 1, wherein the promoter is a heterologous promoter.

5. The expression cassette of claim 1, wherein the one or more heterologous excisable introns are positioned between the promoter and an open reading frame encoding said AAV capsid protein.

6. The expression cassette of claim 1, wherein the one or more heterologous excisable introns comprise at least one splice donor and at least one splice acceptor site.

7. The expression cassette of claim 1, further comprising an AAV intron adjacent to the 3' end of the one of more heterologous excisable introns.

8. The expression cassette of claim 7, wherein the one or more heterologous excisable introns comprise at least one splice donor site and the AAV intron comprises at least one splice acceptor site.

9. A vector comprising the expression cassette of claim 1.

10. A cell comprising the expression cassette of claim 1.

11. A method of generating an expression cassette for producing adeno-associated virus (AAV) vectors, comprising inserting one or more heterologous excisable introns into a polynucleotide comprising a nucleic acid molecule encoding an AAV capsid protein operably linked to a promoter and a polyadenylation signal, wherein said nucleic acid molecule has a length of less than 5 kilobases, and wherein said nucleic acid molecule and said one or more heterologous excisable introns together have a length of more than 5 kilobases, and
wherein the total size of the one or more heterologous excisable introns together is at least 2 kb.

12. The method of claim 11, wherein the one or more heterologous excisable introns are positioned between the promoter and an open reading frame encoding said AAV capsid protein.

* * * * *

SEQUENCE LISTING

```
<160> NUMBER OF SEQ ID NOS: 19

<210> SEQ ID NO 1
<211> LENGTH: 2211
<212> TYPE: DNA
<213> ORGANISM: Adeno-associated virus 6
<220> FEATURE:
<221> NAME/KEY: CDS
<222> LOCATION: (1)..(2211)

<400> SEQUENCE: 1 atg gct gcc gat ggt tat ctt cca gat tgg ctc gag gac aac ctc tct      48
Met Ala Ala Asp Gly Tyr Leu Pro Asp Trp Leu Glu Asp Asn Leu Ser
1               5                   10                  15 gag ggc att cgc gag tgg tgg gac ttg aaa cct gga gcc ccg aaa ccc      96
Glu Gly Ile Arg Glu Trp Trp Asp Leu Lys Pro Gly Ala Pro Lys Pro
            20                  25                  30 aaa gcc aac cag caa aag cag gac gac ggc cgg ggt ctg gtg ctt cct     144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
    50                  55                  60
```

-continued

| | |
|---|---|
| gtc aac gcg gcg gat gca gcg gcc ctc gag cac gac aag gcc tac gac<br>Val Asn Ala Ala Asp Ala Ala Ala Leu Glu His Asp Lys Ala Tyr Asp<br>65                      70                          75                        80 | 240 |
| cag cag ctc aaa gcg ggt gac aat ccg tac ctg cgg tat aac cac gcc<br>Gln Gln Leu Lys Ala Gly Asp Asn Pro Tyr Leu Arg Tyr Asn His Ala<br>                    85                        90                        95 | 288 |
| gac gcc gag ttt cag gag cgt ctg caa gaa gat acg tct ttt ggg ggc<br>Asp Ala Glu Phe Gln Glu Arg Leu Gln Glu Asp Thr Ser Phe Gly Gly<br>                100                      105                      110 | 336 |
| aac ctc ggg cga gca gtc ttc cag gcc aag aag agg gtt ctc gaa cct<br>Asn Leu Gly Arg Ala Val Phe Gln Ala Lys Lys Arg Val Leu Glu Pro<br>        115                      120                      125 | 384 |
| ttt ggt ctg gtt gag gaa ggt gct aag acg gct cct gga aag aaa cgt<br>Phe Gly Leu Val Glu Glu Gly Ala Lys Thr Ala Pro Gly Lys Lys Arg<br>130                      135                          140 | 432 |
| ccg gta gag cag tcg cca caa gag cca gac tcc tcc tcg ggc att ggc<br>Pro Val Glu Gln Ser Pro Gln Glu Pro Asp Ser Ser Ser Gly Ile Gly<br>145                      150                      155                      160 | 480 |
| aag aca ggc cag cag ccc gct aaa aag aga ctc aat ttt ggt cag act<br>Lys Thr Gly Gln Gln Pro Ala Lys Lys Arg Leu Asn Phe Gly Gln Thr<br>                  165                      170                      175 | 528 |
| ggc gac tca gag tca gtc ccc gac cca caa cct ctc gga gaa cct cca<br>Gly Asp Ser Glu Ser Val Pro Asp Pro Gln Pro Leu Gly Glu Pro Pro<br>        180                      185                      190 | 576 |
| gca acc ccc gct gct gtg gga cct act aca atg gct tca ggc ggt ggc<br>Ala Thr Pro Ala Ala Val Gly Pro Thr Thr Met Ala Ser Gly Gly Gly<br>195                      200                      205 | 624 |
| gca cca atg gca gac aat aac gaa ggc gcc gac gga gtg ggt aat gcc<br>Ala Pro Met Ala Asp Asn Asn Glu Gly Ala Asp Gly Val Gly Asn Ala<br>     210                      215                      220 | 672 |
| tca gga aat tgg cat tgc gat tcc aca tgg ctg ggc gac aga gtc atc<br>Ser Gly Asn Trp His Cys Asp Ser Thr Trp Leu Gly Asp Arg Val Ile<br>225                      230                      235                      240 | 720 |
| acc acc agc acc cga aca tgg gcc ttg ccc acc tat aac aac cac ctc<br>Thr Thr Ser Thr Arg Thr Trp Ala Leu Pro Thr Tyr Asn Asn His Leu<br>                245                      250                      255 | 768 |
| tac aag caa atc tcc agt gct tca acg ggg gcc agc aac gac aac cac<br>Tyr Lys Gln Ile Ser Ser Ala Ser Thr Gly Ala Ser Asn Asp Asn His<br>        260                      265                      270 | 816 |
| tac ttc ggc tac agc acc ccc tgg ggg tat ttt gat ttc aac aga ttc<br>Tyr Phe Gly Tyr Ser Thr Pro Trp Gly Tyr Phe Asp Phe Asn Arg Phe<br>275                      280                      285 | 864 |
| cac tgc cat ttc tca cca cgt gac tgg cag cga ctc atc aac aac aat<br>His Cys His Phe Ser Pro Arg Asp Trp Gln Arg Leu Ile Asn Asn Asn<br>     290                      295                      300 | 912 |
| tgg gga ttc cgg ccc aag aga ctc aac ttc aag ctc ttc aac atc caa<br>Trp Gly Phe Arg Pro Lys Arg Leu Asn Phe Lys Leu Phe Asn Ile Gln<br>305                      310                      315                      320 | 960 |
| gtc aag gag gtc acg acg aat gat ggc gtc acg acc atc gct aat aac<br>Val Lys Glu Val Thr Thr Asn Asp Gly Val Thr Thr Ile Ala Asn Asn<br>                325                      330                      335 | 1008 |
| ctt acc agc acg gtt caa gtc ttc tcg gac tcg gag tac cag ttg ccg<br>Leu Thr Ser Thr Val Gln Val Phe Ser Asp Ser Glu Tyr Gln Leu Pro<br>        340                      345                      350 | 1056 |
| tac gtc ctc ggc tct gcg cac cag ggc tgc ctc cct ccg ttc ccg gcg<br>Tyr Val Leu Gly Ser Ala His Gln Gly Cys Leu Pro Pro Phe Pro Ala<br>355                      360                      365 | 1104 |
| gac gtg ttc atg att ccg cag tac ggc tac cta acg ctc aac aat ggc<br>Asp Val Phe Met Ile Pro Gln Tyr Gly Tyr Leu Thr Leu Asn Asn Gly<br>     370                      375                      380 | 1152 |

-continued

| | | |
|---|---|---|
| agc cag gca gtg gga cgg tca tcc ttt tac tgc ctg gaa tat ttc cca<br>Ser Gln Ala Val Gly Arg Ser Ser Phe Tyr Cys Leu Glu Tyr Phe Pro<br>385                              390                       395                  400 | 1200 |
| tcg cag atg ctg aga acg ggc aat aac ttt acc ttc agc tac acc ttc<br>Ser Gln Met Leu Arg Thr Gly Asn Asn Phe Thr Phe Ser Tyr Thr Phe<br>                      405                        410                       415 | 1248 |
| gag gac gtg cct ttc cac agc agc tac gcg cac agc cag agc ctg gac<br>Glu Asp Val Pro Phe His Ser Ser Tyr Ala His Ser Gln Ser Leu Asp<br>                 420                       425                      430 | 1296 |
| cgg ctg atg aat cct ctc atc gac cag tac ctg tat tac ctg aac aga<br>Arg Leu Met Asn Pro Leu Ile Asp Gln Tyr Leu Tyr Tyr Leu Asn Arg<br>435                              440                       445 | 1344 |
| act cag aat cag tcc gga agt gcc caa aac aag gac ttg ctg ttt agc<br>Thr Gln Asn Gln Ser Gly Ser Ala Gln Asn Lys Asp Leu Leu Phe Ser<br>      450                       455                       460 | 1392 |
| cgg ggg tct cca gct ggc atg tct gtt cag ccc aaa aac tgg cta cct<br>Arg Gly Ser Pro Ala Gly Met Ser Val Gln Pro Lys Asn Trp Leu Pro<br>465                              470                       475                  480 | 1440 |
| gga ccc tgt tac cgg cag cag cgc gtt tct aaa aca aaa aca gac aac<br>Gly Pro Cys Tyr Arg Gln Gln Arg Val Ser Lys Thr Lys Thr Asp Asn<br>                      485                       490                      495 | 1488 |
| aac aac agc aac ttt acc tgg act ggt gct tca aaa tat aac ctt aat<br>Asn Asn Ser Asn Phe Thr Trp Thr Gly Ala Ser Lys Tyr Asn Leu Asn<br>            500                       505                       510 | 1536 |
| ggg cgt gaa tct ata atc aac cct ggc act gct atg gcc tca cac aaa<br>Gly Arg Glu Ser Ile Ile Asn Pro Gly Thr Ala Met Ala Ser His Lys<br>515                              520                       525 | 1584 |
| gac gac aaa gac aag ttc ttt ccc atg agc ggt gtc atg att ttt gga<br>Asp Asp Lys Asp Lys Phe Phe Pro Met Ser Gly Val Met Ile Phe Gly<br>      530                       535                       540 | 1632 |
| aag gag agc gcc gga gct tca aac act gca ttg gac aat gtc atg atc<br>Lys Glu Ser Ala Gly Ala Ser Asn Thr Ala Leu Asp Asn Val Met Ile<br>545                              550                       555                  560 | 1680 |
| aca gac gaa gag gaa atc aaa gcc act aac ccc gtg gcc acc gaa aga<br>Thr Asp Glu Glu Glu Ile Lys Ala Thr Asn Pro Val Ala Thr Glu Arg<br>                 565                       570                      575 | 1728 |
| ttt ggg act gtg gca gtc aat ctc cag agc agc agc aca gac cct gcg<br>Phe Gly Thr Val Ala Val Asn Leu Gln Ser Ser Ser Thr Asp Pro Ala<br>            580                       585                       590 | 1776 |
| acc gga gat gtg cat gtt atg gga gcc tta cct gga atg gtg tgg caa<br>Thr Gly Asp Val His Val Met Gly Ala Leu Pro Gly Met Val Trp Gln<br>595                              600                       605 | 1824 |
| gac aga gac gta tac ctg cag ggt cct att tgg gcc aaa att cct cac<br>Asp Arg Asp Val Tyr Leu Gln Gly Pro Ile Trp Ala Lys Ile Pro His<br>      610                       615                       620 | 1872 |
| acg gat gga cac ttt cac ccg tct cct ctc atg ggc ggc ttt gga ctt<br>Thr Asp Gly His Phe His Pro Ser Pro Leu Met Gly Gly Phe Gly Leu<br>625                              630                       635                  640 | 1920 |
| aag cac ccg cct cct cag atc ctc atc aaa aac acg cct gtt cct gcg<br>Lys His Pro Pro Pro Gln Ile Leu Ile Lys Asn Thr Pro Val Pro Ala<br>                 645                       650                      655 | 1968 |
| aat cct ccg gca gag ttt tcg gct aca aag ttt gct tca ttc atc acc<br>Asn Pro Pro Ala Glu Phe Ser Ala Thr Lys Phe Ala Ser Phe Ile Thr<br>            660                       665                       670 | 2016 |
| cag tat tcc aca gga caa gtg agc gtg gag att gaa tgg gag ctg cag<br>Gln Tyr Ser Thr Gly Gln Val Ser Val Glu Ile Glu Trp Glu Leu Gln<br>675                              680                       685 | 2064 |
| aaa gaa aac agc aaa cgc tgg aat ccc gaa gtg cag tat aca tct aac<br>Lys Glu Asn Ser Lys Arg Trp Asn Pro Glu Val Gln Tyr Thr Ser Asn<br>      690                       695                       700 | 2112 |

-continued

| | | | | | | | | | | | | | | | |
|---|---|---|---|---|---|---|---|---|---|---|---|---|---|---|---|
| tat | gca | aaa | tct | gcc | aac | gtt | gat | ttc | act | gtg | gac | aac | aat | gga | ctt | 2160
| Tyr | Ala | Lys | Ser | Ala | Asn | Val | Asp | Phe | Thr | Val | Asp | Asn | Asn | Gly | Leu |
| 705 | | | | 710 | | | | | 715 | | | | | 720 | |
| tat | act | gag | cct | cgc | ccc | att | ggc | acc | cgt | tac | ctc | acc | cgt | ccc | ctg | 2208
| Tyr | Thr | Glu | Pro | Arg | Pro | Ile | Gly | Thr | Arg | Tyr | Leu | Thr | Arg | Pro | Leu |
| | | 725 | | | | | 730 | | | | | 735 | | | |
| taa | | | | | | | | | | | | | | | | 2211

<210> SEQ ID NO 2
<211> LENGTH: 736
<212> TYPE: PRT
<213> ORGANISM: Adeno-associated virus 6

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

-continued

Val Lys Glu Val Thr Thr Asn Asp Gly Val Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

```
<210> SEQ ID NO 3
<211> LENGTH: 31
<212> TYPE: DNA
<213> ORGANISM: Artificial Sequence
<220> FEATURE:
<223> OTHER INFORMATION: Synthetic

<400> SEQUENCE: 3
ggtatggctg ccgatggtta tcttccagat t                            31

<210> SEQ ID NO 4
<211> LENGTH: 325
<212> TYPE: DNA
<213> ORGANISM: Artificial Sequence
<220> FEATURE:
<223> OTHER INFORMATION: Synthetic

<400> SEQUENCE: 4
accaaaacaa atgttctcgt cacgcgggca tgcttcagat gctgtttccc tgcaaaacat    60
gcgagagaat gaatcagaat ttcaacattt gcttcacgca cgggaccaga gactgttcag   120
aatgtttccc cggcgtgtca gaatctcaac cggtcgtcag aaagaggacg tatcggaaac   180
tctgtgccat tcatcatctg ctggggcggg ctcccgagat tgcttgctcg gcctgcgatc   240
tggtcaacgt ggatctggat gactgtgttt ctgagcaata aatgacttaa accaggtatg   300
gctgccgatg gttatcttcc agatt                                         325

<210> SEQ ID NO 5
<211> LENGTH: 4286
<212> TYPE: DNA
<213> ORGANISM: Artificial Sequence
<220> FEATURE:
<223> OTHER INFORMATION: Synthetic

<400> SEQUENCE: 5
gcgcggtgga gtgagcgaag cgcacgctga ggaggatcgg cggccggtga ggggaagca     60 agtctggtct ctgtgattga agaagtcggc tctgggctcc agtgcgggaa tcacacacat   120
acctcaggtg actaatccca agctcggttt ctccaggaac tcactttggt ttgtgtccag   180
tgacatgggt gttcgagagc gggtaggccc cgggctaata cctcccttc ccgtccctgc    240 gcgggaagtg gctggacagc accgccacca cccgcgctgt cgtgggcctc ctcgccggct   300
ccgtgtaggt catcctgtgt tccagaggca tcgttgttcg agcagaggaa tctcgtgaag   360
gaaagtgggc cgagtggatt gtacagcctc tacaatatgc cgaaagtgag aatgccatga   420
cgatggggcg gtctcaggag aacgctgtga caccgtaact cttaacccg gctcaggacg    480 ctgagcactt tgcttttttcc aggcttgaga attccatctt ttcttccgcc caacagctc   540 taccaaaaat ttcccctgcg tctcagtgga aaccaaactg gcctcttacc tgagaaacct   600
gtgggacggg caccgtgttg aaagagcgg ggtccgagta gttttcatc tgataattga     660 atgagtcacc ccttgaacca aaactaaatg agacttgagt ttattactgt tactatcagt   720
ttgtcgtatt ttggcgacaa tgagaataga actgtgttaa gcatatgtta ggttaactat   780
gttagttaag cataactaaa acctaagata aggatatatt tcgggttaa atacacagtc    840 atgctgaggt ctctttatcc tcaaaactta ggcttttaa attttatta agcaaaaaac     900 atggtttctt cgagaaaaag tatagcagag aagtctttat ttcccctcaa ttgagttgtt   960
attcaaggaa caatctctgt caatagtttg ggggtgactt gtacagaact ttgctaccta  1020
ttcttagttc atctggtgcc aaaagatgta gttgtctcat gcacagtaat gtttgtagag  1080
```

```
attcggtgat aactttcttt ttcaactata atgatgaaat aaaagcttta cttatgtagc      1140
actcctatac caagaactag cattcagaga gcattcctaa tacgtgttag atccaaatta      1200
gaattatcac gagagttgtc cccatcacat aatatatttt ggaaaggaat gtgaacttct      1260
atatccatta tagcagtttg accatgcact gttttgagaa agaagtccta cctaccattt      1320
gtcatgcaaa ataactgact atgcagggta tttgaaatta gcctggagtt tggttgatat      1380
attttgaaag gtggctgata cttttttacat cagaacacat aagagtatta tagcatgttg      1440
tgatattgag gttctgtggg ttaaagacat tctggatttg atgtcggatt acttgagttt      1500
agctcctacg ctagtactta ttaagcattt gttcttaagg aagtattata atttagtatt      1560
tctgttccac cttttcctgtt cattgcttca ctgtgcccctt tcatagtact ttgtattgta      1620
attatttgct tgctagtttg tttcccactc tatacttaat tacttaggta agagtctttt      1680 tttttttttct tttttctttt ttctttttttt ttttgagaca gagtctctgt tgcccaggct      1740
ggagtgtagt ggcacgatct cagctcactg tagcctctgc ccctgggttc aagggattct      1800
cctgcctcag ccactatagt agtgggatta caggtgcctg ccaccacacc cagctaattt      1860 tggtatttttt agtagaaatg gggtttcacc atgttgacca ggctggcctc gaactcctgg      1920
tttcaagtga tccacccgcc tcggcctccc aaagtgctgg gattacaggt gtgagccact      1980
gcgcctggcc tggtaagagt cttttcttgtt gtatcattag tgcttagtac atagtagcta      2040
ctgaaaaaaa aattaacaaa ttattatatt acaaaatgga aatacctttct ttttcttttca      2100 atatttttatg tttgactagc acataatggt tttcaaaatg ttttttacgta tacatgtgat      2160 accctcagta aacctgtgat gtacatggca cagatgagaa actacagttc aaaggatgtt      2220
atctttccca agcagccact tctagtaagt agcagagcaa ggactggaac acaaggctag      2280
agttgttccc cgagtttact atgttaattg cctgatttga cacttcttga ggaccaaata      2340
aaataagaat gctgtgaaaa agataaagag gtgaagtcac ctagtgtgac ttcgatattg      2400
cggaatgatt tttttaagtt aaaaaaaaaa tttaagttat tagcatttca ttaggcaata      2460
tgttcaaaaa ttgtcaacca atatgcaggt ttttgtggta tggattctttt ttgtacttaa      2520 ctactatcta tctttactat gaataacata ccatcaacag tattcctttta cttaccctttt      2580 atgttgcaaa gagacttgtg cctcctgaag aaatagtatt catagtcata tcccttcagg      2640
attctcttac atgattgccc atgtttttta accatcaaat taagccttgc ttcccctaaa      2700
agcatcacct ttactgtttg gagaagcttg gtaagtaaat gtggttttca ctggtcaaat      2760
gtcttgcaac tgttccatac atttctgtaa catagtttat ttttatgccc aatttgaaac      2820 ttttttagctc tcaaatttga gagctttaca tacacatatt caacaacagt ttccccaccc      2880
ccaccctcga aaagccctgt ttaaaaacga aacaaacagt cagctgtttc ttggtgggta      2940
aggccattga atgtctactt ctctttattt gctaaatccc tattttgtag ggattttgta      3000
ttccctacaa agaaatacat ctctgctact gtcattaata tgctgctctt tgttgtcaaa      3060
cagatgagta ctaatagttt gcacttattg gtgttatgta ctctggcact gaatatatat      3120
taatgttgct ttttaagtaa aatgtttcta attataatat atttatgaat agttttgaga      3180
gaatatagtc ttactgataa gaggacagac tctggatcca gacttcatgg attcaaatcc      3240
tgactcatca cctgttagca gtatgtgaaa gaacaagtaa cttaacctgt gcttcagttt      3300
tttaatctat aaaatgggga gaactaggga gaaagttgta ccacaaggag ataggcaatg      3360
gccagatcat ataggattct gtaggtagtg gaaagataca taagtcagtg ggaagccact      3420
gagaagatat aggcaggtgc caattaataa gttattatat gaattttcac aaggttttct      3480
```

| | |
|---|---|
| taggcctttta agttctgtta ctacctacgt tttgagcagt gacaacagtg aaggttaaca | 3540 |
| gaaaaacatg aaaatcatca gccatgatta gtttgagagc ttccttttt aaatatgctt | 3600 |
| ctacccaggc tatgatttca ggcttgtgga tcataaaagg agtagtgctg aaagtaggtt | 3660 |
| gggtggatca aagggaataa ttgtaaatat ctttaatgct tggaggttaa gagaaacttg | 3720 |
| aactttgtag taatggagat taaagctatt ctcaagatta ggtataccta ttcaataaaa | 3780 |
| gaaaggaata tttgggagta ttggggataa gagaagctag acattgtgaa ttcaaggaaa | 3840 |
| aagaattatg agaggaggat gcattttagt ttattttgtg attaaaattt ttttagtttt | 3900 |
| tgttgttttg acatgtgaca ctgtaatttt ggctataata aatgacagaa tgtatcattt | 3960 |
| ggtatattgg ttagggttta ggtagaaaat tttttccttt atatagtgag tggtagcgta | 4020 |
| tacaatgttt gctcacttcg gcaaagagta gctttagttt tctgattagt tataatagtg | 4080 |
| atgcttccca tcatttgata tgccttaaag tagtatttta ctcttgaggt attcctttaa | 4140 |
| tccttaggtc ttggagtact ttatagatgg tcattatttt ttatgattcc tctgaaacta | 4200 |
| aaggcagaga atcacccaag cattacaaaa atgttgagca aataaaaat taaagcttgg | 4260 |
| ttcctgaaca ttatctgttt tctggt | 4286 |

<210> SEQ ID NO 6
<211> LENGTH: 2293
<212> TYPE: DNA
<213> ORGANISM: Artificial Sequence
<220> FEATURE:
<223> OTHER INFORMATION: Synthetic

<400> SEQUENCE: 6

| | |
|---|---|
| ggtatggctg ccgatggtta tcttccagat tggctcgagg acaacctctc tgagggcatt | 60 |
| cgcgagtggt gggacttgaa acctggagcc ccgaaaccca agccaaccca gcaaaagcag | 120 |
| gacgacggcc ggggtctggt gcttcctggc tacaagtacc tcggaccctt caacggactc | 180 |
| gacaagggg agcccgtcaa cgcggcggat gcagcggccc tcgagcacga caaggcctac | 240 |
| gaccagcagc tcaaagcggg tgacaatccg tacctgcggt ataaccacgc cgacgccgag | 300 |
| tttcaggagc gtctgcaaga agatacgtct tttgggggca acctcggcg agcagtcttc | 360 |
| caggccaaga gagggttct cgaacctttt ggtctggttg aggaaggtgc taagacggct | 420 |
| cctggaaaga aacgtccggt agagcagtcg ccacaagagc cagactcctc ctcgggcatt | 480 |
| ggcaagacag gccagcagcc cgctaaaaag agactcaatt ttggtcagac tggcgactca | 540 |
| gagtcagtcc ccgacccaca acctctcgga gaacctccag caaccccgc tgctgtggga | 600 |
| cctactacaa tggcttcagg cggtggcgca ccaatggcag acaataacga aggcgccgac | 660 |
| ggagtgggta atgcctcagg aaattggcat gcgattcca catggctggg cgacagagtc | 720 |
| atcaccacca gcacccgaac atgggcttg cccacctata caaccacct ctacaagcaa | 780 |
| atctccagtg cttcaacggg ggccagcaac gacaaccact acttcggcta cagcacccc | 840 |
| tgggggtatt ttgatttcaa cagattccac tgccatttct caccacgtga ctggcagcga | 900 |
| ctcatcaaca caattgggg attccggccc aagagactca acttcaagct cttcaacatc | 960 |
| caagtcaagg aggtcacgac gaatgatggc gtcacgacca tcgctaataa ccttaccagc | 1020 |
| acggttcaag tcttctcgga ctcggagtac cagttgccgt acgtcctcgg ctctgcgcac | 1080 |
| cagggctgcc tccctccgtt cccggcggac gtgttcatga ttccgcagta cggctaccta | 1140 |
| acgctcaaca atggcagcca ggcagtggga cggtcatcct tttactgcct ggaatatttc | 1200 |
| ccatcgcaga tgctgagaac gggcaataac tttaccttca gctacacctt cgaggacgtg | 1260 |

```
cctttccaca gcagctacgc gcacagccag agcctggacc ggctgatgaa tcctctcatc   1320
gaccagtacc tgtattacct gaacagaact cagaatcagt ccggaagtgc ccaaaacaag   1380
gacttgctgt ttagccgggg gtctccagct ggcatgtctg ttcagcccaa aaactggcta   1440
cctggaccct gttaccggca gcagcgcgtt tctaaaacaa aaacagacaa caacaacagc   1500
aactttacct ggactggtgc ttcaaaatat aaccttaatg ggcgtgaatc tataatcaac   1560
cctggcactg ctatggcctc acacaaagac gacaaagaca agttctttcc catgagcggt   1620
gtcatgattt ttggaaagga gagcgccgga gcttcaaaca ctgcattgga caatgtcatg   1680
atcacagacg aagaggaaat caaagccact aaccccgtgg ccaccgaaag atttgggact   1740
gtggcagtca atctccagag cagcagcaca gaccctgcga ccggagatgt gcatgttatg   1800
ggagccttac ctggaatggt gtggcaagac agagacgtat acctgcaggg tcctatttgg   1860
gccaaaattc ctcacacgga tggacacttt caccegtctc ctctcatggg cggctttgga   1920
cttaagcacc cgcctcctca gatcctcatc aaaaacacgc ctgttcctgc gaatcctccg   1980
gcagagtttt cggctacaaa gtttgcttca ttcatcaccc agtattccac aggacaagtg   2040
agcgtggaga ttgaatggga gctgcagaaa gaaaacagca acgctggaa tcccgaagtg   2100 cagtatacat ctaactatgc aaaatctgcc aacgttgatt tcactgtgga caacaatgga   2160
ctttatactg agcctcgccc cattggcacc cgttacctca cccgtcccct gtaattgtgt   2220
gttaatcaat aaaccggtta attcgtgtca gttgaacttt ggtctcatgt cgttattatc   2280
ttatctggtc acc                                                      2293

<210> SEQ ID NO 7
<211> LENGTH: 9761
<212> TYPE: DNA
<213> ORGANISM: Artificial Sequence
<220> FEATURE:
<223> OTHER INFORMATION: Synthetic

<400> SEQUENCE: 7
cctcgaagcg gccgccgcgg cctcgaggag cttgccattg catacgttgt atccatatca     60
taatatgtac atttatattg gctcatgtcc aacattaccg ccatgttgac attgattatt    120
gactagttat taatagtaat caattacggg gtcattagtt catagcccat atatggagtt    180
ccgcgttaca taacttacgg taaatggccc gcctggctga ccgcccaacg acccccgccc    240
attgacgtca ataatgacgt atgttcccat agtaacgcca tagggacttt ccattgacg    300 tcaatgggtg gagtatttac ggtaaactgc ccacttggca gtacatcaag tgtatcatat    360
gccaagtacg ccccctattg acgtcaatga cggtaaatgg cccgcctggc attatgccca    420
gtacatgacc ttatgggact ttcctacttg gcagtacatc tacgtattag tcatcgctat    480
taccatggtg atgcggtttt ggcagtacat caatgggcgt ggatagcggt ttgactcacg    540
gggatttcca agtctccacc ccattgacgt caatgggagt ttgttttggc accaaaatca    600
acgggacttt ccaaaatgtc gtaacaactc cgccccattg acgcaaatgg gcggtaggcg    660
tgtacggtgg gaggtctata taagcagagc tcgtttagtg aaccgtcaga tcgcctggag    720
acgccatcca cgctgttttg acctccatag aagacaccgg accgatccag cctccccgg    780 aagctagcgc ggtggagtga cgaagcgca cgctgaggag gatcggcggc cggtgagggg    840
gaagcaagtc tggtctctgt gattgaagaa gtcggctctg gctccagtg cgggaatcac    900 acacatacct caggtgacta atcccaagct cggtttctcc aggaactcac tttggtttgt    960
gtccagtgac atgggtgttc gagagcgggt aggccccggg ctaatacctc cctttcccgt   1020
```

```
ccctgcgcgg gaagtggctg dacagcaccg ccaccacccg cgctgtcgtg ggcctcctcg   1080
ccggctccgt gtaggtcatc ctgtgttcca gaggcatcgt tgttcgagca gaggaatctc   1140
gtgaaggaaa gtgggccgag tggattgtac agcctctaca atatgccgaa agtgagaatg   1200
ccatgacgat ggggcggtct caggagaacg ctgtgacacc gtaactctta accccggctc   1260
aggacgctga gcactttgct ttttccaggc ttgagaattc catcttttct tccgcccaa    1320 cagctctacc aaaaatttcc cctgcgtctc agtggaaacc aaactggcct cttacctgag   1380
aaacctgtgg gacgggcacc gtgttggaaa gagcgggtc cgagtagttt ttcatctgat    1440
aattgaatga gtcaccccctt gaaccaaaac taaatgagac ttgagtttat tactgttact   1500
atcagtttgt cgtattttgg cgacaatgag aatagaactg tgttaagcat atgttaggtt   1560
aactatgtta gttaagcata actaaaacct aagataagga tatattttcg ggttaaatac   1620
acagtcatgc tgaggtctct ttatcctcaa aacttaggct ttttaaattt ttattaagca   1680
aaaaacatgg tttcttcgag aaaaagtata gcagagaagt ctttatttcc cctcaattga   1740
gttgttattc aaggaacaat ctctgtcaat agtttggggg tgacttgtac agaactttgc   1800
tacctattct tagttcatct ggtgccaaaa gatgtagttg tctcatgcac agtaatgttt   1860
gtagagattc ggtgataact ttcttttca actataatga tgaaataaaa gctttactta   1920
tgtagcactc ctataccaag aactagcatt cagagagcat tcctaatacg tgttagatcc   1980
aaattagaat tatcacgaga gttgtcccca tcacataata tattttggaa aggaatgtga   2040
acttctatat ccattatagc agtttgacca tgcactgttt tgagaaagaa gtcctaccta   2100
ccatttgtca tgcaaaataa ctgactatgc agggtatttg aaattagcct ggagtttggt   2160
tgatatattt tgaaaggtgg ctgatacttt ttacatcaga acacataaga gtattatagc   2220
atgttgtgat attgaggttc tgtgggttaa agacattctg gatttgatgt cggattactt   2280
gagtttagct cctacgctag tacttattaa gcatttgttc ttaaggaagt attataattt   2340
agtatttctg ttccaccttt cctgttcatt gcttcactgt gcccttcat agtactttgt     2400 attgtaatta tttgcttgct agtttgtttc ccactctata cttaattact taggtaagag   2460 tcttttttt ttttctttt tctttttct ttttttttt gagacagagt ctctgttgcc       2520
caggctggag tgtagtggca cgatctcagc tcactgtagc ctctgcccct gggttcaagg   2580
gattctcctg cctcagccac tatagtagtg ggattacagg tgcctgccac cacacccagc   2640
taattttggt atttttagta gaaatggggt ttcaccatgt tgaccaggct ggcctcgaac   2700
tcctggtttc aagtgatcca cccgcctcgg cctcccaaag tgctgggatt acaggtgtga   2760
gccactgcgc ctggcctggt aagagtcttt cttgttgtat cattagtgct tagtacatag   2820
tagctactga aaaaaaatt aacaaattat tatattacaa aatggaaata ccttcttttt    2880 cttcaatat tttatgtttg actagcacat aatggttttc aaaatgtttt tacgtataca    2940
tgtgataccc tcagtaaacc tgtgatgtac atggcacaga tgagaaacta cagttcaaag   3000
gatgttatct ttcccaagca gccacttcta gtaagtagca gagcaaggac tggaacacaa   3060
ggctagagtt gttccccgag tttactatgt taattgcctg atttgacact tcttgaggac   3120
caaataaaat aagaatgctg tgaaaaagat aaagaggtga agtcacctag tgtgacttcg   3180
atattgcgga atgatttttt taagttaaaa aaaaatttta agttattagc atttcattag   3240
gcaatatgtt caaaaattgt caaccaatat gcaggttttt gtggtatgga ttcttttgt    3300 acttaactac tatctatctt tactatgaat aacataccat caacagtatt cctttactta   3360
ccctttatgt tgcaaagaga cttgtgcctc ctgaagaaat agtattcata gtcatatccc   3420
```

```
ttcaggattc tcttacatga ttgcccatgt tttttaacca tcaaattaag ccttgcttcc    3480
cctaaaagca tcacctttac tgtttggaga agcttggtaa gtaaatgtgg ttttcactgg    3540
tcaaatgtct tgcaactgtt ccatacattt ctgtaacata gtttattttt atgcccaatt    3600
tgaaactttt tagctctcaa atttgagagc tttacataca catattcaac aacagtttcc    3660 ccaccccac cctcgaaaag ccctgtttaa aaacgaaaca aacagtcagc tgtttcttgg     3720
tgggtaaggc cattgaatgt ctacttctct ttatttgcta aatccctatt ttgtagggat    3780
tttgtattcc ctacaaagaa atacatctct gctactgtca ttaatatgct gctctttgtt    3840
gtcaaacaga tgagtactaa tagttttgcac ttattggtgt tatgtactct ggcactgaat   3900
atatattaat gttgcttttt aagtaaaatg tttctaatta taatatattt atgaatagtt    3960
ttgagagaat atagtcttac tgataagagg acagactctg gatccagact tcatggattc    4020
aaatcctgac tcatcacctg ttagcagtat gtgaaagaac aagtaactta acctgtgctt    4080 cagttttta atctataaaa tggggagaac tagggagaaa gttgtaccac aaggagatag     4140
gcaatggcca gatcatatag gattctgtag gtagtggaaa gatacataag tcagtgggaa    4200
gccactgaga agatataggc aggtgccaat taataagtta ttatatgaat tttcacaagg    4260
ttttcttagg cctttaagtt ctgttactac ctacgttttg agcagtgaca acagtgaagg    4320
ttaacagaaa aacatgaaaa tcatcagcca tgattagttt gagagcttcc tttttttaaat   4380 atgcttctac ccaggctatg atttcaggct tgtggatcat aaaaggagta gtgctgaaag    4440
taggttgggt ggatcaaagg gaataattgt aaatatcttt aatgcttgga ggttaagaga    4500
aacttgaact ttgtagtaat ggagattaaa gctattctca agattaggta tacctattca    4560
ataaaagaaa ggaatatttg ggagtattgg ggataagaga agctagacat tgtgaattca    4620
aggaaaaaga attatgagag gaggatgcat tttagtttat tttgtgatta aaattttttt    4680 agttttgtt gttttgacat gtgacactgt aattttggct ataataaatg acagaatgta    4740
tcatttggta tattggttag ggtttaggta gaaaatttt tcctttatat agtgagtggt     4800
agcgtataca atgtttgctc acttcggcaa agagtagctt tagttttctg attagttata    4860
atagtgatgc ttcccatcat ttgatatgcc ttaaagtagt attttactct tgaggtattc    4920
ctttaatcct taggtcttgg agtactttat agatggtcat tattttttat gattcctctg    4980
aaactaaagg cagagaatca cccaagcatt acaaaatgt tgagcaaaat aaaaattaaa     5040
gcttggttcc tgaacattat ctgttttctg gtaccaaaac aaatgttctc gtcacgcggg    5100
catgcttcag atgctgtttc cctgcaaaac atgcgagaga atgaatcaga atttcaacat    5160
ttgcttcacg cacgggacca gagactgttc agaatgtttc cccggcgtgt cagaatctca    5220
accggtcgtc agaagaggga cgtatcggaa actctgtgcc attcatcatc tgctggggcg    5280
ggctcccgag attgcttgct cggcctgcga tctggtcaac gtggatctgg atgactgtgt    5340
ttctgagcaa taaatgactt aaaccaggta tggctgccga tggttatctt ccagattggc    5400
tcgaggacaa cctctctgag ggcattcgcg agtggtggga cttgaaacct ggagccccga    5460
aacccaaagc caaccagcaa agcaggacg acggccgggg tctggtgctt cctggctaca    5520
agtacctcgg acccttcaac ggactcgaca agggggagcc cgtcaacgcg gcggatgcag    5580
cggccctcga gcacgacaag gcctacgacc agcagctcaa agcgggtgac aatccgtacc    5640
tgcggtataa ccacgccgac gccgagtttc aggagcgtct gcaagaagat acgtcttttg    5700
ggggcaacct cggcgagca gtcttccagg ccaagaagag ggttctcgaa ccttttggtc     5760
tggttgagga aggtgctaag acggctcctg gaaagaaacg tccggtagag cagtcgccac    5820
```

```
aagagccaga ctcctcctcg ggcattggca agacaggcca gcagcccgct aaaaagagac    5880
tcaattttgg tcagactggc gactcagagt cagtccccga cccacaacct ctcggagaac    5940
ctccagcaac ccccgctgct gtgggaccta ctacaatggc ttcaggcggt ggcgcaccaa    6000
tggcagacaa taacgaaggc gccgacggag tgggtaatgc ctcaggaaat tggcattgcg    6060
attccacatg gctgggcgac agagtcatca ccaccagcac ccgaacatgg gccttgccca    6120
cctataacaa ccacctctac aagcaaatct ccagtgcttc aacggggggcc agcaacgaca    6180 accactactt cggctacagc acccccctggg ggtatttga tttcaacaga ttccactgcc    6240
atttctcacc acgtgactgg cagcgactca tcaacaacaa ttggggattc cggcccaaga    6300
gactcaactt caagctcttc aacatccaag tcaaggaggt cacgacgaat gatggcgtca    6360
cgaccatcgc taataacctt accagcacgg ttcaagtctt ctcggactcg gagtaccagt    6420
tgccgtacgt cctcggctct gcgcaccagg gctgcctccc tccgttcccg gcggacgtgt    6480
tcatgattcc gcagtacggc tacctaacgc tcaacaatgg cagccaggca gtgggacggt    6540
catcctttta ctgcctggaa tatttcccat cgcagatgct gagaacgggc aataacttta    6600
ccttcagcta caccttcgag gacgtgcctt tccacagcag ctacgcgcac agccagagcc    6660
tggaccggct gatgaatcct ctcatcgacc agtacctgta ttacctgaac agaactcaga    6720
atcagtccgg aagtgcccaa aacaaggact tgctgtttag ccggggggtct ccagctggca    6780 tgtctgttca gcccaaaaac tggctacctg gaccctgtta ccggcagcag cgcgtttcta    6840
aaacaaaaac agacaacaac aacagcaact ttacctggac tggtgcttca aaatataacc    6900
ttaatgggcg tgaatctata atcaaccctg gcactgctat ggcctcacac aaagacgaca    6960
aagacaagtt cttccccatg agcggtgtca tgattttgg aaaggagagc gccggagctt    7020
caaacactgc attggacaat gtcatgatca cagacgaaga ggaaatcaaa gccactaacc    7080
ccgtggccac cgaaagattt gggactgtgg cagtcaatct ccagagcagc agcacagacc    7140
ctgcgaccga agatgtgcat gttatgggag ccttacctgg aatggtgtgg caagacagag    7200
acgtatacct gcagggtcct atttgggcca aaattcctca cacggatgga cactttcacc    7260
cgtctcctct catgggcggc tttggactta agcacccgcc tcctcagatc ctcatcaaaa    7320
acacgcctgt tcctgcgaat cctccggcag agttttcggc tacaaagttt gcttcattca    7380
tcacccagta ttccacagga caagtgagcg tggagattga atgggagctg cagaaagaaa    7440
acagcaaacg ctggaatccc gaagtgcagt atacatctaa ctatgcaaaa tctgccaacg    7500
ttgatttcac tgtggacaac aatggacttt tatactgagcc tcgccccatt ggcacccgtt    7560
acctcacccg tcccctgtaa ttgtgtgtta atcaataaac cggttaattc gtgtcagttg    7620
aactttggtc tcatgtcgtt attatcttat ctggtcacca gatccccggg taccgaggat    7680
ctaacttgtt tattgcagct tataatggtt acaaataaag caatagcatc acaaatttca    7740
caaataaagc attttttttca ctgcattcta gttgtggttt gtccaaactc atcaatgtat    7800
cttatcatgt ctggatccgg ccgcggcggc gcgatccga cgcgaggctg gatggccttc    7860
cccattatga ttcttctcgc ttccggcggc atcgggatgc ccgcgttgca ggccatgctg    7920
tccaggcagg tagatgacga ccatcaggga cagcttcaaa aaggccagca aaaggccagg    7980
aaccgtaaaa aggccgcgtt gctggcgttt ttccataggc tccgcccccc tgacgagcat    8040
cacaaaaatc gacgctcaag tcagaggtgg cgaaacccga caggactata aagataccag    8100
gcgtttcccc ctggaagctc cctcgtgcgc tctcctgttc cgaccctgcc gcttaccgga    8160
tacctgtccg cctttctccc ttcgggaagc gtggcgcttt ctcatagctc acgctgtagg    8220
```

-continued

```
tatctcagtt cggtgtaggt cgttcgctcc aagctgggct gtgtgcacga accccccgtt      8280
cagcccgacc gctgcgcctt atccggtaac tatcgtcttg agtccaaccc ggtaagacac      8340
gacttatcgc cactggcagc agccactggt aacaggatta gcagagcgag gtatgtaggc      8400
ggtgctacag agttcttgaa gtggtggcct aactacggct acactagaag gacagtattt      8460
ggtatctgcg ctctgctgaa gccagttacc ttcggaaaaa gagttggtag ctcttgatcc      8520
ggcaaacaaa ccaccgctgg tagcggtggt ttttttgttt gcaagcagca gattacgcgc      8580
agaaaaaaag gatctcaaga gatcctttg atcttttcta cggggtctga cgctcagtgg      8640
aacgaaaact cacgttaagg gattttggtc atgagattat caaaaaggat cttcacctag      8700
atccttttaa attaaaaatg aagttttaaa tcaatctaaa gtatatatga gtaaacttgg      8760
tctgacagtt accaatgctt aatcagtgag gcacctatct cagcgatctg tctatttcgt      8820
tcatccatag ttgcctgact ccccgtcgtg tagataacta cgatacggga gggcttacca      8880
tctggcccca gtgctgcaat gataccgcga gacccacgct caccggctcc agatttatca      8940
gcaataaacc agccagccgg aagggccgag cgcagaagtg gtcctgcaac tttatccgcc      9000
tccatccagt ctattaattg ttgccgggaa gctagagtaa gtagttcgcc agttaatagt      9060
ttgcgcaacg ttgttgccat tgctgcaggc atcgtggtgt cacgctcgtc gtttggtatg      9120
gcttcattca gctccggttc ccaacgatca aggcgagtta catgatcccc catgttgtgc      9180
aaaaaagcgg ttagctcctt cggtcctccg atcgttgtca gaagtaagtt ggccgcagtg      9240
ttatcactca tggttatggc agcactgcat aattctctta ctgtcatgcc atccgtaaga      9300
tgcttttctg tgactggtga gtactcaacc aagtcattct gagaatagtg tatgcggcga      9360
ccgagttgct cttgcccggc gtcaacacgg gataataccg cgccacatag cagaacttta      9420
aaagtgctca tcattggaaa acgttcttcg ggcgaaaac tctcaaggat cttaccgctg      9480
ttgagatcca gttcgatgta acccactcgt gcacccaact gatcttcagc atcttttact      9540
ttcaccagcg tttctgggtg agcaaaaaca ggaaggcaaa atgccgcaaa aaagggaata      9600
agggcgacac ggaaatgttg aatactcata ctcttccttt ttcaatatta ttgaagcatt      9660
tatcagggtt attgtctcat gagcggatac atatttgaat gtatttagaa aaataaacaa      9720
ataggggttc cgcgcacatt tccccgaaaa gtgccacctg c                         9761
```

<210> SEQ ID NO 8
<211> LENGTH: 2208
<212> TYPE: DNA
<213> ORGANISM: Adeno-associated virus 2
<220> FEATURE:
<221> NAME/KEY: CDS
<222> LOCATION: (1)..(2208)

<400> SEQUENCE: 8

```
atg gct gcc gat ggt tat ctt cca gat tgg ctc gag gac act ctc tct        48
Met Ala Ala Asp Gly Tyr Leu Pro Asp Trp Leu Glu Asp Thr Leu Ser
1               5                   10                  15 gaa gga ata aga cag tgg tgg aag ctc aaa cct ggc cca cca cca cca        96
Glu Gly Ile Arg Gln Trp Trp Lys Leu Lys Pro Gly Pro Pro Pro Pro
            20                  25                  30 aag ccc gca gag cgg cat aag gac gac agc agg ggt ctt gtg ctt cct       144
Lys Pro Ala Glu Arg His Lys Asp Asp Ser Arg Gly Leu Val Leu Pro
        35                  40                  45 ggg tac aag tac ctc gga ccc ttc aac gga ctc gac aag gga gag ccg       192
Gly Tyr Lys Tyr Leu Gly Pro Phe Asn Gly Leu Asp Lys Gly Glu Pro
    50                  55                  60
```

```
gtc aac gag gca gac gcc gcg gcc ctc gag cac gac aaa gcc tac gac      240
Val Asn Glu Ala Asp Ala Ala Ala Leu Glu His Asp Lys Ala Tyr Asp
 65              70                  75                  80 cgg cag ctc gac agc gga gac aac ccg tac ctc aag tac aac cac gcc      288
Arg Gln Leu Asp Ser Gly Asp Asn Pro Tyr Leu Lys Tyr Asn His Ala
                 85                  90                  95 gac gcg gag ttt cag gag cgc ctt aaa gaa gat acg tct ttt ggg ggc      336
Asp Ala Glu Phe Gln Glu Arg Leu Lys Glu Asp Thr Ser Phe Gly Gly
            100                 105                 110 aac ctc gga cga gca gtc ttc cag gcg aaa aag agg gtt ctt gaa cct      384
Asn Leu Gly Arg Ala Val Phe Gln Ala Lys Lys Arg Val Leu Glu Pro
        115                 120                 125 ctg ggc ctg gtt gag gaa cct gtt aag acg gct ccg gga aaa aag agg      432
Leu Gly Leu Val Glu Glu Pro Val Lys Thr Ala Pro Gly Lys Lys Arg
    130                 135                 140 ccg gta gag cac tct cct gtg gag cca gac tcc tcc tcg gga acc gga      480
Pro Val Glu His Ser Pro Val Glu Pro Asp Ser Ser Ser Gly Thr Gly
145                 150                 155                 160 aag gcg ggc cag cag cct gca aga aaa aga ttg aat ttt ggt cag act      528
Lys Ala Gly Gln Gln Pro Ala Arg Lys Arg Leu Asn Phe Gly Gln Thr
                165                 170                 175 gga gac gca gac tca gta cct gac ccc cag cct ctc gga cag cca cca      576
Gly Asp Ala Asp Ser Val Pro Asp Pro Gln Pro Leu Gly Gln Pro Pro
            180                 185                 190 gca gcc ccc tct ggt ctg gga act aat acg atg gct aca ggc agt ggc      624
Ala Ala Pro Ser Gly Leu Gly Thr Asn Thr Met Ala Thr Gly Ser Gly
        195                 200                 205 gca cca atg gca gac aat aac gag ggc gcc gac gga gtg ggt aat tcc      672
Ala Pro Met Ala Asp Asn Asn Glu Gly Ala Asp Gly Val Gly Asn Ser
    210                 215                 220 tcg gga aat tgg cat tgc gat tcc aca tgg atg ggc gac aga gtc atc      720
Ser Gly Asn Trp His Cys Asp Ser Thr Trp Met Gly Asp Arg Val Ile
225                 230                 235                 240 acc acc agc acc cga acc tgg gcc ctg ccc acc tac aac aac cac ctc      768
Thr Thr Ser Thr Arg Thr Trp Ala Leu Pro Thr Tyr Asn Asn His Leu
                245                 250                 255 tac aaa caa att tcc agc caa tca gga gcc tcg aac gac aat cac tac      816
Tyr Lys Gln Ile Ser Ser Gln Ser Gly Ala Ser Asn Asp Asn His Tyr
            260                 265                 270 ttt ggc tac agc acc cct tgg ggg tat ttt gac ttc aac aga ttc cac      864
Phe Gly Tyr Ser Thr Pro Trp Gly Tyr Phe Asp Phe Asn Arg Phe His
        275                 280                 285 tgc cac ttt tca cca cgt gac tgg caa aga ctc atc aac aac aac tgg      912
Cys His Phe Ser Pro Arg Asp Trp Gln Arg Leu Ile Asn Asn Asn Trp
    290                 295                 300 gga ttc cga ccc aag aga ctc aac ttc aag ctc ttt aac att caa gtc      960
Gly Phe Arg Pro Lys Arg Leu Asn Phe Lys Leu Phe Asn Ile Gln Val
305                 310                 315                 320 aaa gag gtc acg cag aat gac ggt acg acg acg att gcc aat aac ctt     1008
Lys Glu Val Thr Gln Asn Asp Gly Thr Thr Thr Ile Ala Asn Asn Leu
                325                 330                 335 acc agc acg gtt cag gtg ttt act gac tcg gag tac cag ctc ccg tac     1056
Thr Ser Thr Val Gln Val Phe Thr Asp Ser Glu Tyr Gln Leu Pro Tyr
            340                 345                 350 gtc ctc ggc tcg gcg cat caa gga tgc ctc ccg ccg ttc cca gca gac     1104
Val Leu Gly Ser Ala His Gln Gly Cys Leu Pro Pro Phe Pro Ala Asp
        355                 360                 365 gtc ttc atg gtg cca cag tat gga tac ctc acc ctg aac aac ggg agt     1152
Val Phe Met Val Pro Gln Tyr Gly Tyr Leu Thr Leu Asn Asn Gly Ser
    370                 375                 380
```

```
cag gca gta gga cgc tct tca ttt tac tgc ctg gag tac ttt cct tct    1200
Gln Ala Val Gly Arg Ser Ser Phe Tyr Cys Leu Glu Tyr Phe Pro Ser
385                 390                 395                 400 cag atg ctg cgt acc gga aac aac ttt acc ttc agc tac act ttt gag    1248
Gln Met Leu Arg Thr Gly Asn Asn Phe Thr Phe Ser Tyr Thr Phe Glu
            405                 410                 415 gac gtt cct ttc cac agc agc tac gct cac agc cag agt ctg gac cgt    1296
Asp Val Pro Phe His Ser Ser Tyr Ala His Ser Gln Ser Leu Asp Arg
        420                 425                 430 ctc atg aat cct ctc atc gac cag tac ctg tat tac ttg agc aga aca    1344
Leu Met Asn Pro Leu Ile Asp Gln Tyr Leu Tyr Tyr Leu Ser Arg Thr
            435                 440                 445 aac act cca agt gga acc acc acg cag tca agg ctt cag ttt tct cag    1392
Asn Thr Pro Ser Gly Thr Thr Thr Gln Ser Arg Leu Gln Phe Ser Gln
        450                 455                 460 gcc gga gcg agt gac att cgg gac cag tct agg aac tgg ctt cct gga    1440
Ala Gly Ala Ser Asp Ile Arg Asp Gln Ser Arg Asn Trp Leu Pro Gly
465                 470                 475                 480 ccc tgt tac cgc cag cag cga gta tca aag aca tct gcg gat aac aac    1488
Pro Cys Tyr Arg Gln Gln Arg Val Ser Lys Thr Ser Ala Asp Asn Asn
            485                 490                 495 aac agt gaa tac tcg tgg act gga gct acc aag tac cac ctc aat ggc    1536
Asn Ser Glu Tyr Ser Trp Thr Gly Ala Thr Lys Tyr His Leu Asn Gly
        500                 505                 510 aga gac tct ctg gtg aat ccg ggc ccg gcc atg gca agc cac aag gac    1584
Arg Asp Ser Leu Val Asn Pro Gly Pro Ala Met Ala Ser His Lys Asp
            515                 520                 525 gat gaa gaa aag ttt ttt cct cag agc ggg gtt ctc atc ttt ggg aag    1632
Asp Glu Glu Lys Phe Phe Pro Gln Ser Gly Val Leu Ile Phe Gly Lys
        530                 535                 540 caa ggc tca gag aaa aca aat gtg gac att gaa aag gtc atg att aca    1680
Gln Gly Ser Glu Lys Thr Asn Val Asp Ile Glu Lys Val Met Ile Thr
545                 550                 555                 560 gac gaa gag gaa atc agg aca acc aat ccc gtg gct acg gag cag tat    1728
Asp Glu Glu Glu Ile Arg Thr Thr Asn Pro Val Ala Thr Glu Gln Tyr
            565                 570                 575 ggt tct gta tct acc aac ctc cag aga ggc aac aga caa gca gct acc    1776
Gly Ser Val Ser Thr Asn Leu Gln Arg Gly Asn Arg Gln Ala Ala Thr
        580                 585                 590 gca gat gtc aac aca caa ggc gtt ctt cca ggc atg gtc tgg cag gac    1824
Ala Asp Val Asn Thr Gln Gly Val Leu Pro Gly Met Val Trp Gln Asp
            595                 600                 605 aga gat gtg tac ctt cag ggg ccc atc tgg gca aag att cca cac acg    1872
Arg Asp Val Tyr Leu Gln Gly Pro Ile Trp Ala Lys Ile Pro His Thr
        610                 615                 620 gac gga cat ttt cac ccc tct ccc ctc atg ggt gga ttc gga ctt aaa    1920
Asp Gly His Phe His Pro Ser Pro Leu Met Gly Gly Phe Gly Leu Lys
625                 630                 635                 640 cac cct cct cca cag att ctc atc aag aac acc ccg gta cct gcg aat    1968
His Pro Pro Pro Gln Ile Leu Ile Lys Asn Thr Pro Val Pro Ala Asn
            645                 650                 655 cct tcg acc acc ttc agt gcg gca aag ttt gct tcc ttc atc aca cag    2016
Pro Ser Thr Thr Phe Ser Ala Ala Lys Phe Ala Ser Phe Ile Thr Gln
        660                 665                 670 tac tcc acg gga cag gtc agc gtg gag atc gag tgg gag ctg cag aag    2064
Tyr Ser Thr Gly Gln Val Ser Val Glu Ile Glu Trp Glu Leu Gln Lys
            675                 680                 685 gaa aac agc aaa cgc tgg aat ccc gaa att cag tac act tcc aac tac    2112
Glu Asn Ser Lys Arg Trp Asn Pro Glu Ile Gln Tyr Thr Ser Asn Tyr
        690                 695                 700
```

-continued

```
aac aag tct gtt aat gtg gac ttt act gtg gac act aat ggc gtg tat        2160
Asn Lys Ser Val Asn Val Asp Phe Thr Val Asp Thr Asn Gly Val Tyr
705                 710                 715                 720 tca gag cct cgc ccc att ggc acc aga tac ctg act cgt aat ctg taa        2208
Ser Glu Pro Arg Pro Ile Gly Thr Arg Tyr Leu Thr Arg Asn Leu
                725                 730                 735
```

<210> SEQ ID NO 9
<211> LENGTH: 735
<212> TYPE: PRT
<213> ORGANISM: Adeno-associated virus 2

<400> SEQUENCE: 9

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

```
Thr Ser Thr Val Gln Val Phe Thr Asp Ser Glu Tyr Gln Leu Pro Tyr
                340                 345                 350

Val Leu Gly Ser Ala His Gln Gly Cys Leu Pro Phe Pro Ala Asp
        355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 10
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 10 cggggttttta cgagattgtg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
cgccatttct ggtctttgtg                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ccacaagagc cagactcctc                                               20

<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13
gccatcattc gtcgtgacc                                                19

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14
ccactgtatt gagcctgatg ttaaa                                         25

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
gctctgtatg ttccctcttc tcggt                                         25

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gcgttaactc ggcgtttcat                                               20
```

```
<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
gcgctcaggt caaattcaga c                                                  21

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
ggctagcgcg gtggagtgag cgaag                                              25

<210> SEQ ID NO 19
<211> LENGTH: 27
<212> TYPE: DNA
<213> ORGANISM: Artificial Sequence
<220> FEATURE:
<223> OTHER INFORMATION: Synthetic

<400> SEQUENCE: 19
ggctagcttc tgcaatttaa acaaaag                                            27
```